US008042547B2

(12) United States Patent
Goldstein

(10) Patent No.: US 8,042,547 B2
(45) Date of Patent: Oct. 25, 2011

(54) RESPIRATORY SHIELD

(76) Inventor: Joseph Goldstein, Los Angeles, CA (US)

( * ) Notice: Subject to any disclaimer, the term of this patent is extended or adjusted under 35 U.S.C. 154(b) by 0 days.

(21) Appl. No.: 12/840,140

(22) Filed: Jul. 20, 2010

(65) Prior Publication Data

US 2011/0114099 A1     May 19, 2011

Related U.S. Application Data

(60) Provisional application No. 61/281,280, filed on Nov. 16, 2009, provisional application No. 61/338,129, filed on Feb. 16, 2010.

(51) Int. Cl.
*A61M 15/08* (2006.01)
*A61M 16/00* (2006.01)

(52) U.S. Cl. .............. 128/207.18; 128/200.24

(58) Field of Classification Search ............. 128/200.24, 128/204.18, 205.25, 206.21, 206.22, 206.28, 128/207.18, 846–848, 857, 859, 887
See application file for complete search history.

(56) References Cited

U.S. PATENT DOCUMENTS

| | | | |
|---|---|---|---|
| 5,720,302 A | 2/1998 | Belfer | 128/848 |
| 5,810,013 A | 9/1998 | Belfer | 128/848 |
| 5,988,170 A | 11/1999 | Thomas | 128/848 |
| 6,012,455 A | 1/2000 | Goldstein | 128/207.18 |
| 6,062,220 A * | 5/2000 | Whitaker et al. | 128/206.19 |
| 6,571,798 B1 | 6/2003 | Thornton | 128/206.21 |
| 6,675,802 B1 | 1/2004 | Thornton | 128/206.29 |
| 6,926,004 B2 | 8/2005 | Schumacher | 128/206.27 |
| 7,021,312 B2 * | 4/2006 | Cannon | 128/206.29 |
| 7,243,650 B2 * | 7/2007 | Thornton | 128/205.25 |
| 7,406,966 B2 * | 8/2008 | Wondka | 128/207.18 |
| 7,500,480 B2 | 3/2009 | Matula et al. | |
| 7,658,189 B2 | 2/2010 | Davidson et al. | |
| 7,708,017 B2 | 5/2010 | Davidson et al. | |
| 2006/0237017 A1 | 10/2006 | Davidson et al. | |
| 2006/0283461 A1 | 12/2006 | Lubke et al. | |
| 2007/0144525 A1 | 6/2007 | Davidson et al. | |
| 2007/0186930 A1 | 8/2007 | Davidson et al. | |
| 2008/0110469 A1 * | 5/2008 | Weinberg | 128/863 |
| 2008/0149105 A1 | 6/2008 | Matula et al. | |
| 2009/0114229 A1 * | 5/2009 | Frater et al. | 128/206.24 |
| 2009/0120443 A1 | 5/2009 | Matula et al. | |
| 2009/0145435 A1 * | 6/2009 | White et al. | 128/204.17 |
| 2009/0277452 A1 | 11/2009 | Lubke et al. | |
| 2010/0132717 A1 | 6/2010 | Davidson et al. | |

FOREIGN PATENT DOCUMENTS

| | | |
|---|---|---|
| AU | 2004/308536 A1 | 7/2005 |
| AU | 2006/255476 A1 | 12/2006 |
| AU | 2010/214658 A1 | 9/2010 |
| CN | 1901961 A | 1/2007 |
| CN | 1901961 C0 | 1/2007 |
| CN | 1973914 A | 6/2007 |
| CN | 1973914 C0 | 6/2007 |
| CN | 101214402 A0 | 7/2008 |
| CN | 101237902 A | 8/2008 |
| CN | 101479010 A | 7/2009 |
| CN | 101628142 A | 1/2010 |
| CN | 1973914 B | 7/2010 |

(Continued)

*Primary Examiner* — Justine R Yu
*Assistant Examiner* — Rachel T Young
(74) *Attorney, Agent, or Firm* — Crandall Patent Group, LLC; Jerry A. Crandall, Esq.

(57) ABSTRACT

In an embodiment, a respiratory shield is disclosed. The respiratory shield is sized to be coupled with a respiratory device having a nasal air intake member so as to be positioned along an oral airflow axis.

20 Claims, 22 Drawing Sheets

FOREIGN PATENT DOCUMENTS

| | | |
|---|---|---|
| EP | 1701759 A1 | 9/2006 |
| EP | 1890755 A1 | 2/2008 |
| EP | 2035094 A2 | 3/2009 |
| EP | 1701759 A4 | 11/2009 |
| JP | 2000/325481 A | 11/2000 |
| JP | 2007/516750 A | 6/2007 |
| JP | 2008-541955 A | 11/2008 |
| JP | 2009/540881 A | 11/2009 |
| NZ | 547748 A | 7/2010 |
| WO | WO 2005/063328 A1 | 7/2005 |
| WO | WO 2006/130903 A1 | 12/2006 |
| WO | WO 2007/147088 A2 | 12/2007 |
| WO | WO 2007/147088 A3 | 12/2007 |
| WO | WO 2007/147088 A3 | 8/2008 |

\* cited by examiner

RESPIRATORY SHIELD

CROSS-REFERENCE TO RELATED APPLICATIONS

This application claims the benefit of U.S. Provisional Application No. 61/281,280, filed on Nov. 16, 2009, and U.S. Provisional Application No. 61/338,129, filed on Feb. 16, 2010, which are incorporated herein by reference in their entirety.

TECHNICAL FIELD

The present technology relates to the field of respiratory devices having nasal air intake members.

BACKGROUND

For a multitude of respiratory ailments, such as, but not limited to, snoring and sleep apnea, the utilization of various ventilation techniques may be implemented for the transmission of oxygen and/or other gases from the nostrils to a patient's upper airway so as to aid with inhalation and exhalation. Continuous positive air pressure (CPAP), or a variation thereof, is an example of such a regimen.

SUMMARY

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter.

In an embodiment, a respiratory shield is disclosed. The respiratory shield is sized to be coupled with a respiratory device having a nasal air intake member so as to be positioned along an oral airflow axis.

Additionally, in one embodiment, a respiratory shield is disclosed, wherein the respiratory shield may include or comprise a base member, an airflow resistor, and a rigid extension associated with the airflow resistor and the base member. The respiratory shield may also include or comprise a force exerting member associated with the base member and the rigid extension, wherein the force exerting member is positioned to exert a force on the rigid extension in a direction toward the airflow resistor.

Moreover, in accordance with an embodiment, a respiratory device is disclosed. The respiratory device may include or comprise a nasal air intake member, and a respiratory shield associated with the nasal air intake member so as to be positioned to resist a degree of airflow through an oral cavity when the nasal air intake member is positioned to direct airflow into a nasal cavity.

DESCRIPTION OF THE DRAWINGS

The accompanying drawings, which are incorporated in and form a part of this specification, illustrate embodiments of the present technology, and, together with the Detailed Description, serve to explain principles discussed below.

Figure 1A:
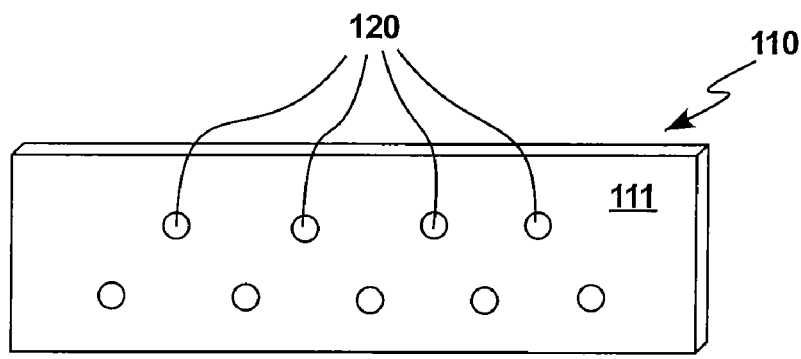
FIGS. 1A and 1B illustrate anterior and perspective views of a first exemplary geometry for a respiratory shield in accordance with an embodiment.

The drawings referred to in this description are not to be understood as being drawn to scale except if specifically noted, and such drawings are only exemplary in nature.

DETAILED DESCRIPTION

Reference will now be made in detail to embodiments of the present technology, examples of which are illustrated in the accompanying drawings. While the present technology will be described in conjunction with various embodiments, these embodiments are not intended to limit the present technology. Rather, the present technology is to be understood as encompassing alternatives, modifications and equivalents, which may be included within the spirit and scope of the various embodiments as defined by the appended claims.

Moreover, in the following Detailed Description numerous specific details are set forth in order to provide a thorough understanding of the present technology. However, the present technology may be practiced without these specific details. In other instances, well-known methods, procedures, components, circuits and devices have not been described in detail so as to not unnecessarily obscure aspects of the exemplary embodiments presented herein.

Furthermore, the term "air" as used herein shall not be limited to any particular gaseous substance. Indeed, the term "air" is meant to refer to any gaseous substance, which may or may not be a mixture of different types of gases.

Overview

In an exemplary scenario, sleep apnea patients, as well as other respiratory patients, may utilize various types of positive air or gaseous pressure systems such as, but not limited to, CPAP, variable positive air pressure (VPAP), bi-level positive air pressure (BIPAP), and automatic positive air pressure (APAP) oxygen generators or ventilators. However, when utilizing such a system, the effectiveness of the respective treatment may suffer if the air that enters through a patient's nostrils escapes through the patient's mouth, rather than entering into the lungs.

An embodiment of the present technology provides a device that can be incorporated into the design of various nasal interfaces, or other oxygen/gas delivering type interfaces, so as to prevent the air that enters through a patient's nostrils from escaping through the patient's mouth. In particular, and to increase the effectiveness of such a treatment, the patient's mouth is closed, sealed or partially sealed so that the pressurized air or gas being delivered into the patient's nostrils for the aforementioned purpose, or for other purposes, does not "short-circuit" outward through the patient's opened mouth.

To illustrate, and in accordance with an embodiment, a respiratory shield is coupled with a respiratory device (e.g. a snoring device). The respiratory shield is sized, and positioned relative to the respiratory device, such that the respiratory shield is configured to be worn outside the mouth, and such that the respiratory shield is configured to seal off a patient's mouth area, either partially (e.g., due to vents, holes or pores defined in the respiratory shield) or completely. Indeed, the respiratory shield may be conformable to a patient's lips so as to efficiently function to restrict airflow through the patient's mouth. Furthermore, the respiratory shield may be configured to be either removable or permanently affixed to a CPAP interface.

It is noted that the present technology has significant utility in the relevant art. For many sleep apnea patients, and for other respiratory patients, who use respiratory devices when sleeping, while opening their mouths, the utilization of a respiratory shield that is worn outside the mouth and is conformable to the user's lips significantly increases the effectiveness of the treatment. Indeed, a respiratory shield as described herein may also be implemented in conjunction with a dental appliance to reduce a patient's snoring.

In addition to the foregoing, an embodiment of the present technology relates to the emission of saliva, and the subsequent absorption thereof, during the utilization of respiratory devices such as, but not limited to, snoring aids and sleep apnea products. In particular, although a non-absorbent mouth shield may be utilized, in many instances during open mouth breathing, with the use of a non-absorbent mouth shield, there is excess salivation and drooling by the patient. Accordingly, absorbent materials, such as, but not limited to, super high absorbing materials of the type utilized in infant diapers and incontinence products, are implemented as or in conjunction with the mouth shield component so that saliva may be absorbed without undue discomfort to the patient.

Various exemplary embodiments of the present technology will now be discussed. It is noted, however, that the present technology is not limited to these exemplary embodiments, and that the present technology also includes obvious variations of the exemplary embodiments and implementations described herein.

Exemplary Structures

Figure 1B:
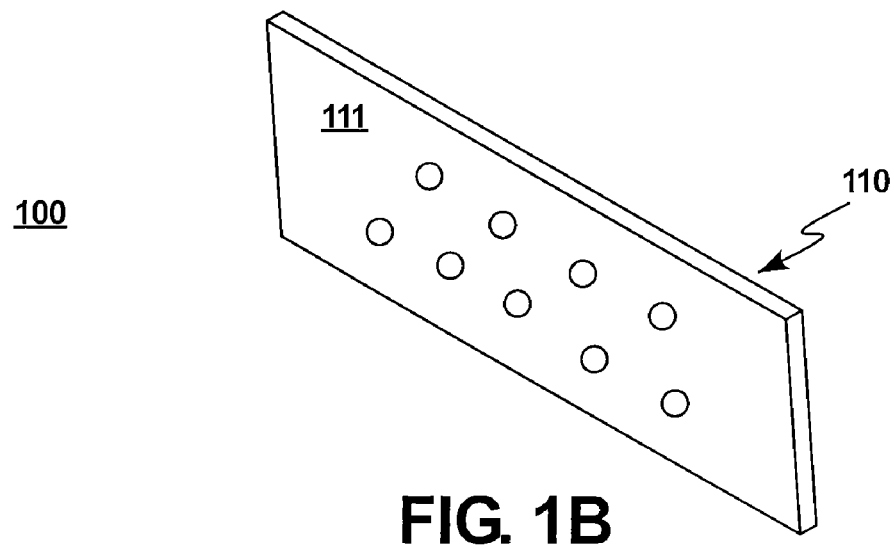

With reference now to FIGS. 1A and 1B, a first exemplary geometry 100 for a respiratory shield 110 in accordance with an embodiment is shown. Respiratory shield 110 includes an airflow resistor 111 sized to be positioned against or adjacent to an oral airflow cavity, such as by being placed against the lip region of a patient's mouth, as will be further discussed herein, so as to resist a degree of airflow through the oral airflow cavity. In this manner, respiratory shield 110 may be coupled, for example, with any of a wide variety of CPAP interfaces (or with other respiratory devices for applications other than sleep apnea) so as to disrupt a degree of oral airflow through a patient's mouth such that airflow through the patient's nasal cavities may be directed into the patient's lungs rather than escaping through the patient's mouth.

It is noted that airflow resistor 111 may be constructed, for example, of soft resilient molded silicone or a hard plastic shell. However, other materials for airflow resistor 111 may also be implemented. Indeed, the present technology is not limited to any particular material for airflow resistor 111 (or any other components described herein).

Pursuant to one embodiment, however, airflow resistor 111 is configured to enable an amount of air to escape from a patient's mouth. To illustrate, an example provides that airflow resistor 111 is substantially flat or non-conforming to the shape of a patient's mouth, such as shown in FIGS. 1A and 1B, which will enable an amount of air to escape from a patient's mouth due to the non-conforming geometry of airflow resistor 111. In a second example, a number of holes, such as pores 120, may be positioned within airflow resistor 111, so as to enable a small amount of airflow through respiratory shield 110. By selecting a particular size for these holes, a degree of airflow through respiratory shield 110 may be both permitted and constrained to a preselected level.

The foregoing notwithstanding, it is noted that although airflow resistor 111, which may be porous or non-porous, is shown in FIGS. 1A and 1B as having a planar geometry, the present technology is not limited to a planar airflow resistor. Indeed, airflow resistor 111 may be adapted to other shapes and sizes.

Figure 2A:
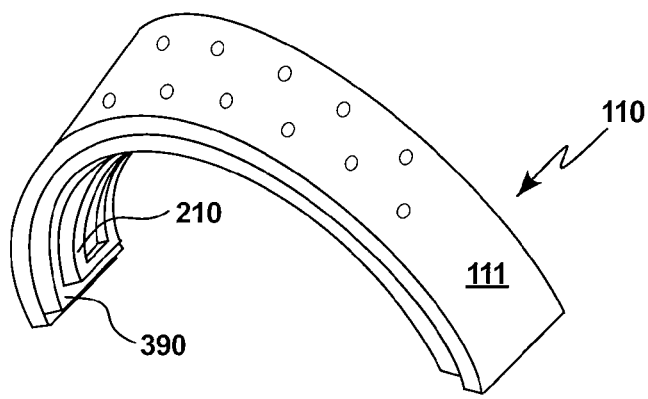
FIGS. 2A-2C illustrate anterior and posterior perspective views of a second exemplary geometry for a respiratory shield in accordance with an embodiment.
Figure 2B:
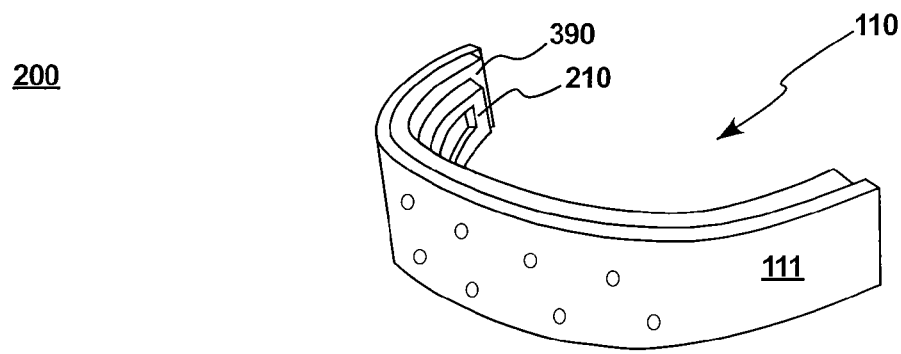
Figure 2C:
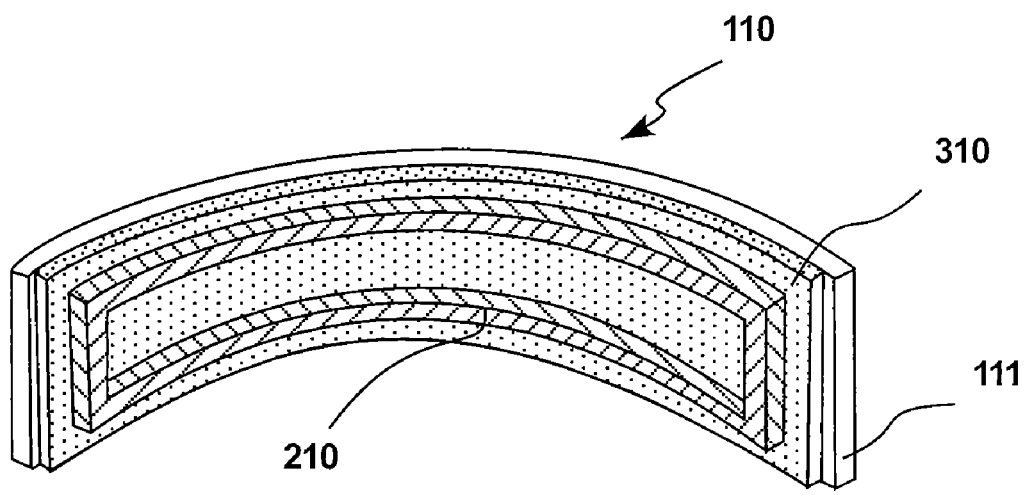

To illustrate, and with reference now to FIGS. 2A-2C, a second exemplary geometry 200 for respiratory shield 110 in accordance with an embodiment is shown. In particular, airflow resistor 111 is shown as being curved rather than planar. In this manner, airflow resistor 111 may be shaped, for example, so as to substantially conform to the outside of a patient's mouth area. It is noted that such a conforming geometry may be beneficial for creating a better seal against a patient's mouth so as to maximize the ability of respiratory shield 110 to resist a degree of airflow through the patient's oral airflow cavity.

It is noted that airflow resistor 111 may also be constructed of a material capable of increasing a patient's comfort level when airflow resistor 111 is held next to a patient's mouth. Consider the example where airflow resistor 111 has no, or extremely minimal, absorption capabilities such that saliva tends to accumulate within respiratory shield 110 while the patient sleeps. This saliva may then escape downward onto the patient's chin causing significant discomfort and skin irritation. Therefore, in one embodiment, airflow resistor 111 includes a liquid absorbent material, which may be beneficial, for example, so as to absorb saliva that seeps out of a patient's mouth when airflow resistor 111 is positioned adjacent thereto.

Furthermore, although airflow resistor 111 may be generally rigid, an embodiment provides that airflow resistor 111 is constructed of an absorbent material capable of absorbing a degree of force such as to provide, for example, a cushioning effect when airflow resistor 111 is pressed against the patient's face which can increase a patient's comfort level. Similarly, in accordance with one embodiment, although airflow resistor 111 may or may not itself be generally rigid, an absorbent material 390 is coupled with airflow resistor 111 such that a similar cushioning effect may be achieved. Moreover, pursuant to one embodiment, absorbent material 390 is a liquid absorbent material configured to absorb an amount of liquid, such as sweat and saliva emitted by a patient.

Moreover, an exemplary implementation provides that a non-water-soluble lubricant, such as Vaseline™, may be implemented to enhance the seal between respiratory shield 110 and a patient's lip region, so as to minimize saliva drip and skin chafing. This lubricant may be supplied within infused disposable pads, such as within absorbent material 390, wherein these pads may be coupled with airflow resistor 111, such as by an adhesive or a fastening member (not shown), such as Velcro™, and replaced during subsequent uses (e.g., nightly) of respiratory shield 110.

Thus, various embodiments provide a device configured to reduce or eliminate the accumulation of sweat and saliva, so as to minimize the discomfort experienced by respiratory patients, through the utilization of materials that have the capability of absorbing moisture. As noted above, respiratory shield 110 may be completely constructed of absorbent materials or utilized in combination with absorbent materials, wherein these materials may be, for example, "high-absorption" and "super-absorbent" materials that "suck up" the saliva, such as due to the natural absorbent characteristics of these materials and the natural viscosity of the liquids at issue. The following are examples of "super-absorbent" materials that may be implemented: Luquafleece™, Gelok™, Gelok™ with a foam laminate, and hydrophilic Ester Foam™. However, these materials are not to be understood as encompassing all possible "super-absorbent" materials.

With reference still to FIGS. 2A-2C, respiratory shield 110, which may be absorbent or non-absorbent, may also include a seal 210 (e.g., an air seal). Consider the example where a shape of both airflow resistor 111 and seal 210 conforms to a shape of a patient's mouth area. Seal 210, which may be constructed, for example, of a soft polymer gel or foam, may be implemented to create an air seal, along its edges, around the patient's mouth. In this manner, the ability of respiratory shield 110 to disrupt airflow through a patient's mouth may be increased.

The foregoing notwithstanding, it is noted that airflow resistor 111 absorbent material 390 and seal 210 are shown in FIGS. 2A-2C as being different components that are coupled together. In one embodiment, however, two or more of these components are formed from a single piece of material, such as where airflow resistor 111 is fabricated to include an air seal that performs the same function as seal 210. Indeed, it is noted that absorbent material 390 and seal 210 are optional components, and that various embodiments of the present technology may therefore be practiced without these components.

Figure 3:
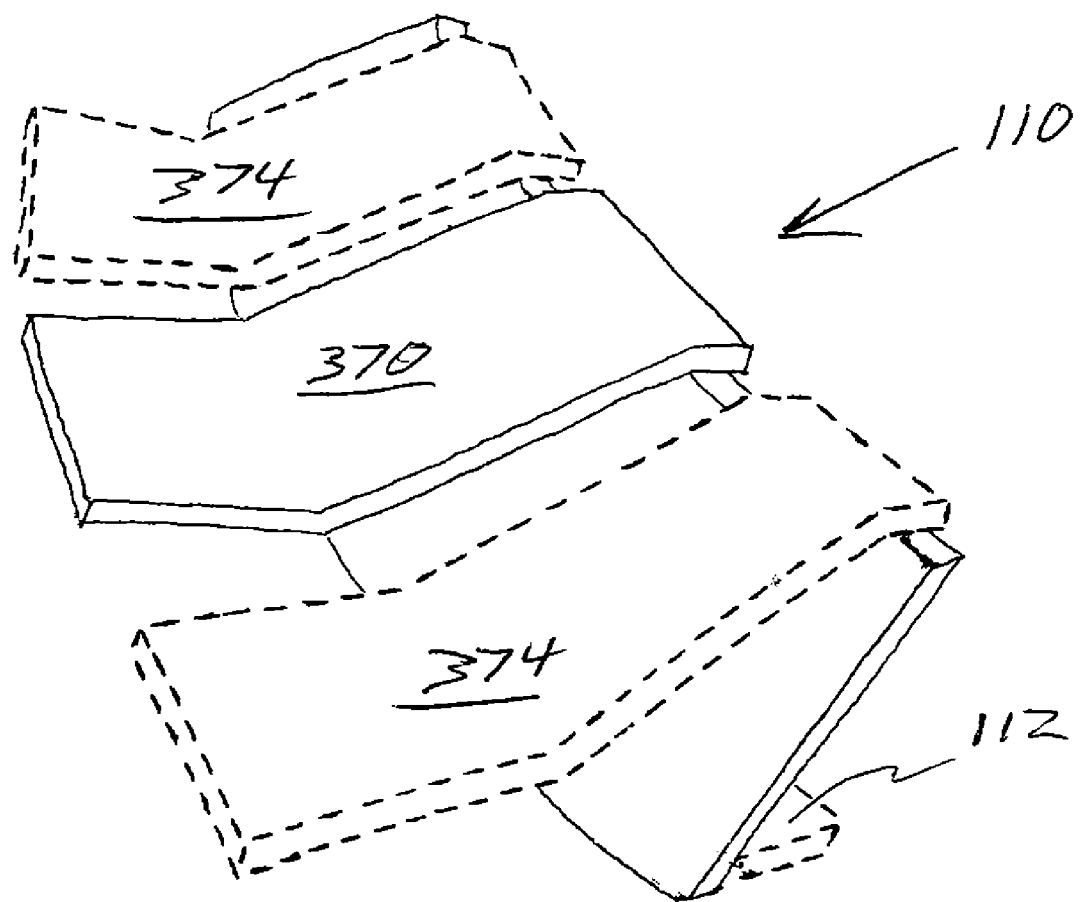
FIG. 3 illustrates a perspective view of a first exemplary configuration for a respiratory shield in accordance with an embodiment.

With reference now to FIG. 3, a first exemplary configuration 1200 for respiratory shield 110 in accordance with an embodiment is shown. Respiratory shield 110 includes an extension 370 coupled with airflow resistor 111, wherein extension 370 is capable of being attached to a respiratory device (not shown) so as to suspend airflow resistor 111 from the respiratory device, as will be further discussed herein. One or more additional extensions 374 may also be coupled with airflow resistor 111, such as to increase a degree of support provided to airflow resistor 111 relative to the respiratory device. It is noted, however, that extension 370, as well as additional extensions 374, are optional components, and that various embodiments of the present technology may therefore be practiced without such components, such as where airflow resistor 111 is directly coupled to a respiratory device.

Moreover, in one embodiment, a secondary shield 112 extends from, or is integrated with or within, airflow resistor 111. For example, secondary shield 112 may be positioned to function as a lower lip cover so as to collect saliva and/or divert saliva back into a patient's mouth. However, similarly to extension 370, it is noted that secondary shield 112 is an optional component, and that various embodiments of the present technology may therefore be practiced without such a component.

Figure 4A:
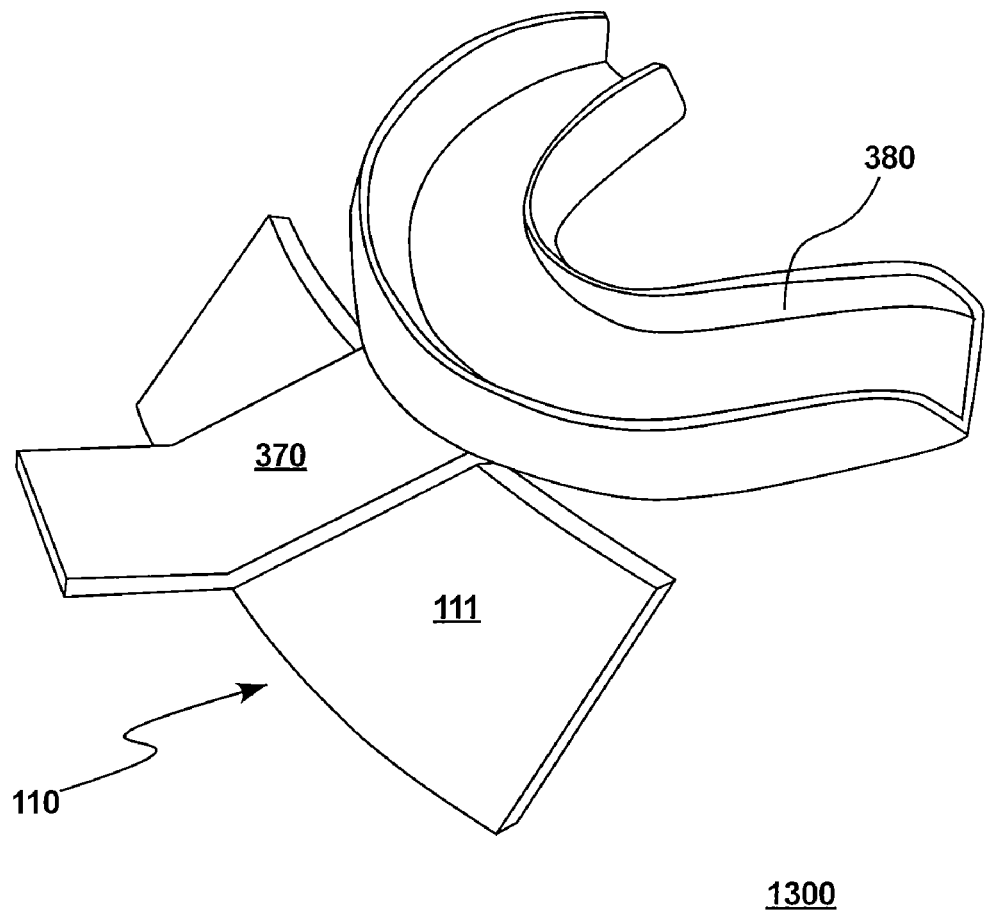
FIGS. 4A-4B illustrate perspective views of a second exemplary configuration for a respiratory shield in accordance with an embodiment.

With reference now to FIG. 4A, a second exemplary configuration 1300 for respiratory shield 110 in accordance with an embodiment is shown. Respiratory shield 110 includes a dental anchor 380 coupled with extension 370 and sized to anchor with a patient's dental region. By tightly anchoring to a portion of a patient's jaw, it is noted that dental anchor 380 enables extension 370 and airflow resistor 111 to be stabilized relative to said jaw.

As shown in FIG. 4A, dental anchor 380 is positioned to anchor with a patient's upper dental jaw region. When a patient's mouth is opened, airflow resistor 111 is positioned to block a degree of airflow through the patient's mouth. As a result, the patient is discouraged from breathing through the mouth, and therefore instead breaths through a nasal cavity.

Figure 4B:
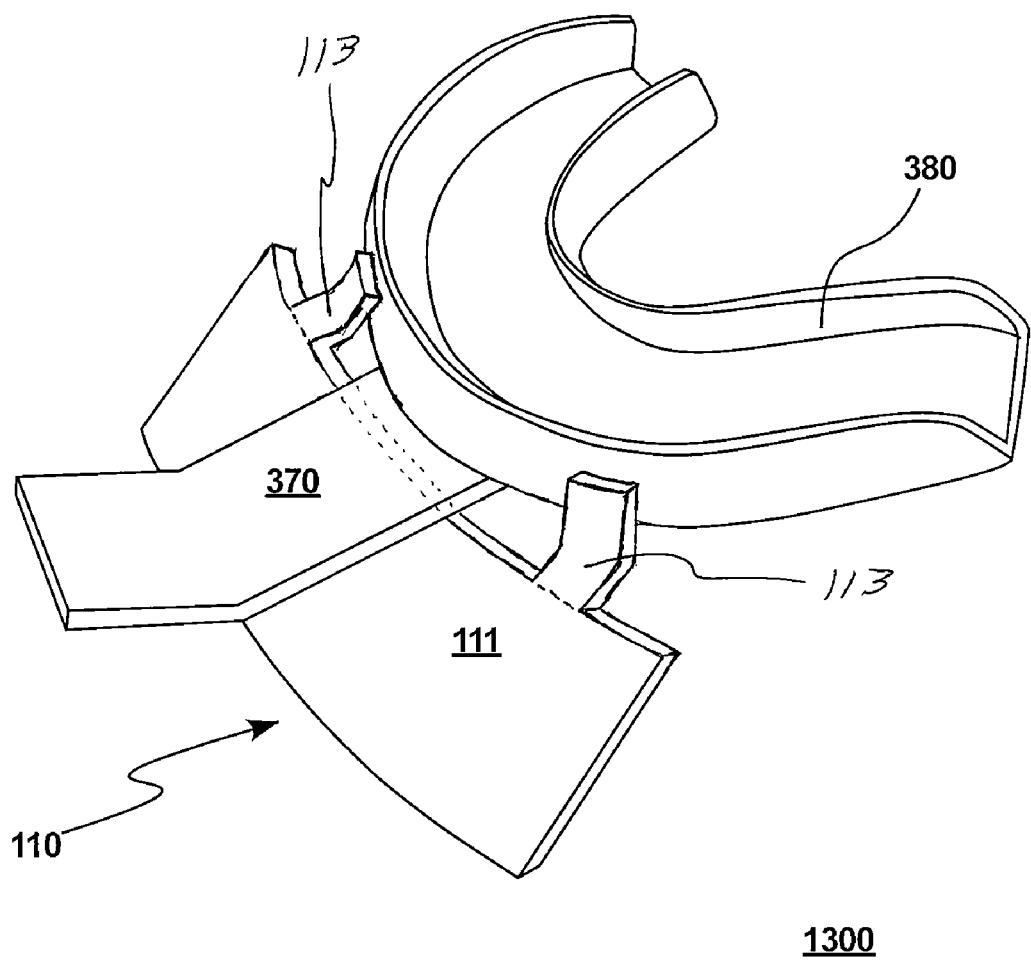

The foregoing notwithstanding, it is noted that other implementations of a dental anchor may also be implemented, and that the present technology is not limited to the specific configuration shown in FIG. 4A. For example, and with reference now to FIG. 4B, an embodiment provides that airflow resistor 111 is coupled to dental anchor 380, such as by optional couplers 113, wherein airflow resistor 111 may be separated from extension 370. Moreover, it is further noted that dental anchor 380 is an optional component, and that various embodiments of the present technology may therefore be practiced without such a component.

Figure 5:
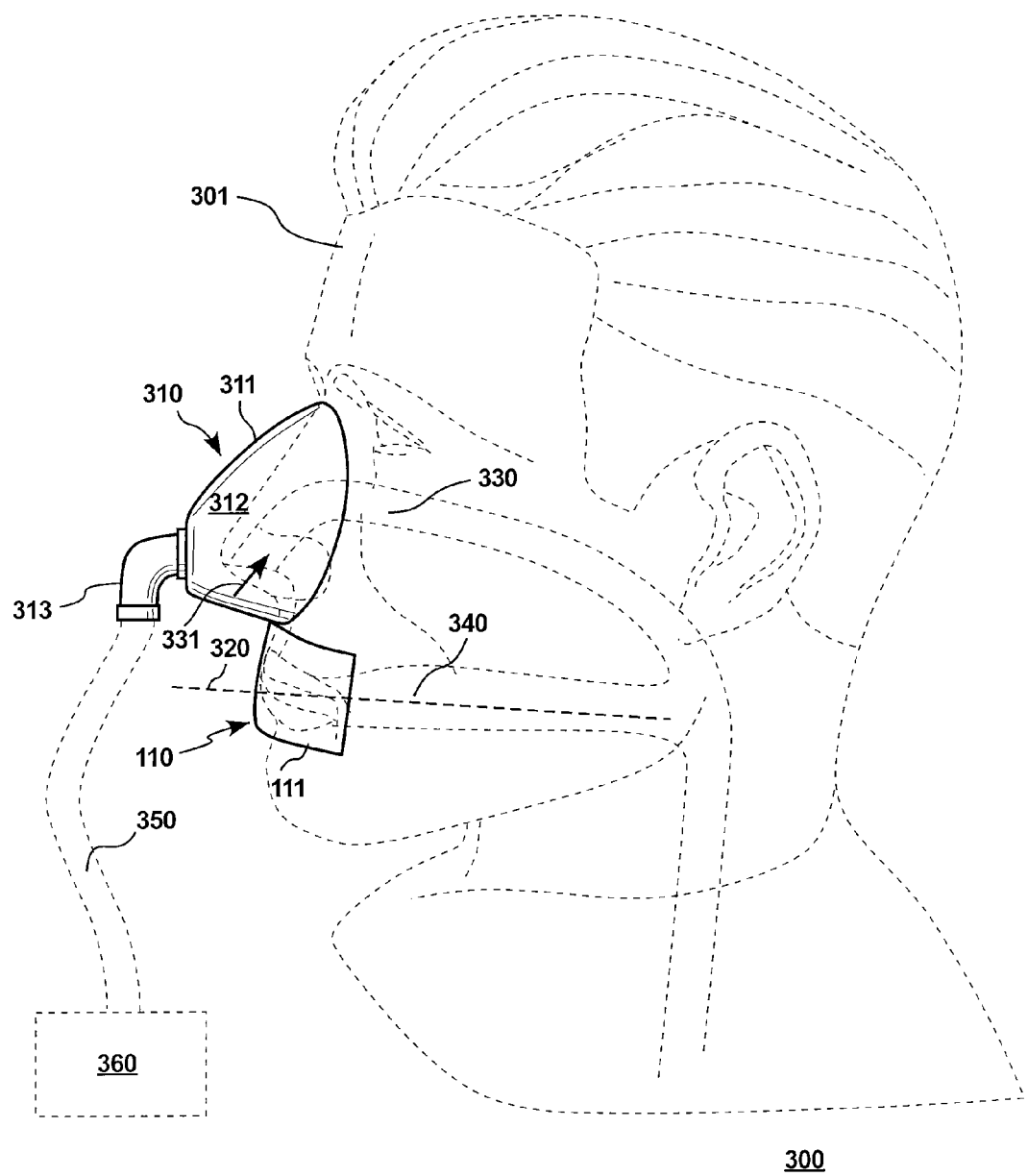
FIG. 5 illustrates a lateral view of a first exemplary respiratory configuration in accordance with an embodiment.

With reference now to FIG. 5, a first exemplary respiratory configuration 300 in accordance with an embodiment is shown. In particular, and for purposes of illustration, first exemplary respiratory configuration 300 shows an exemplary implementation of respiratory shield 110 in regards to a patient 301. First exemplary respiratory configuration 300 includes respiratory shield 110, which is sized to be coupled with a respiratory device 310 having a nasal air intake member 311, so as to be positioned along an oral airflow axis 320 when nasal air intake member 311 is positioned to inject air into a nasal cavity 330 (as represented by arrow 331). Moreover, it is noted that respiratory shield 110 is sized to be coupled with respiratory device 310 so as to be positioned adjacent to an opening of an oral airflow cavity 340 and resist a degree of airflow through oral airflow cavity 340 when nasal air intake member 311 is positioned to direct airflow into nasal cavity 330.

To further illustrate, and with reference still to FIG. 5, an embodiment provides that respiratory shield 110 includes airflow resistor 111, which is sized to be applied against a lip region of oral airflow cavity 340, outside of oral airflow cavity 340, within a preselected pressure range when respiratory shield 110 is coupled with respiratory device 310 and nasal air intake member 311 is positioned to direct airflow into nasal cavity 330. For example, airflow resistor 111, which may be shaped to conform to a patient's mouth, may be of adequate size and shape so as to be pressed against a patient's lips at a pressure that is sufficient to disrupt airflow through the patient's mouth, while not being applied with enough pressure to cause the patient to suffer physical discomfort. Furthermore, it is noted that one or more optional couplers, such as optional couplers 113 shown in FIG. 4B, may be implemented to couple airflow resistor 111 with nasal air intake member 311.

Thus, an embodiment provides that respiratory device 310, which includes nasal air intake member 311, either includes or is integrated with respiratory shield 110, wherein respiratory shield 110 is coupled with and extends from nasal air intake member 311, and wherein respiratory shield 110 is positioned relative to nasal air intake member 311 so as to resist a degree of airflow through oral airflow cavity 340 when nasal air intake member 311 is positioned to direct airflow into nasal cavity 330. It is noted that respiratory shield 110 may be permanently coupled with nasal air intake member 311. In one embodiment, however, a removable shield is provided, wherein respiratory shield 110 is configured to be removed from, and subsequently reattached to, respiratory device 310.

It is noted that the present technology is not limited to any particular type of respiratory device or nasal air intake member. For example, as shown in FIG. 5, nasal air intake member 311 includes a contoured mask 312, which may be sized to conform to a patient's face so as to enclose a patient's nose (but not a patient's mouth). Nasal air intake member 311 may also include a coupling member 313 coupled with or extending from contoured mask 312, wherein coupling member 313 is sized to couple with a hose 350, which may be attached to a gas or air supply 360. However, other types of respiratory devices and nasal air intake members may also be implemented.

Moreover, and notwithstanding the exemplary configuration shown in FIG. 5, it is noted that airflow resistor 111, which may be resilient or non-resilient against a patient's face, may be sized to cover the bottom portion of a patient's open mouth, or may instead cover both upper and lower portions of the open mouth (as shown). Thus, it is noted that airflow resistor 111 may be sized to cover all or a portion of a mouth area, and that the present technology is not limited to any particular size of airflow resistor 111 or implementation thereof.

Furthermore, it is noted that placing an air seal inside a patient's mouth, behind the patient's lips, may cause a degree of discomfort during sleep. In particular, such discomfort may result, for example, from a foreign object being placed behind the patient's lips that is large enough to prevent air flow through the patient's mouth cavity. In one embodiment, however, a respiratory shield as described herein is sized so as to be worn outside a patient's mouth so as to increase a patient's level of comfort, such as shown in FIG. 5. For example, the respiratory shield may be coupled with and extend from a nasal air intake member to a degree that the respiratory shield is pushed against the patient's mouth, outside of the patient's lips, at a pressure sufficient to prevent a degree of exhalation through the patient's mouth. This novel configuration of extending a respiratory shield from a nasal intake member so as to achieve this specific level of pressure outside of the patient's mouth, such that the patient does not endure the discomfort associated with having such a respiratory shield placed inside the mouth area, would not be obvious in view of an air seal that extends, for example, from a dental appliance, and which is worn behind the patient's lips.

Figure 6:
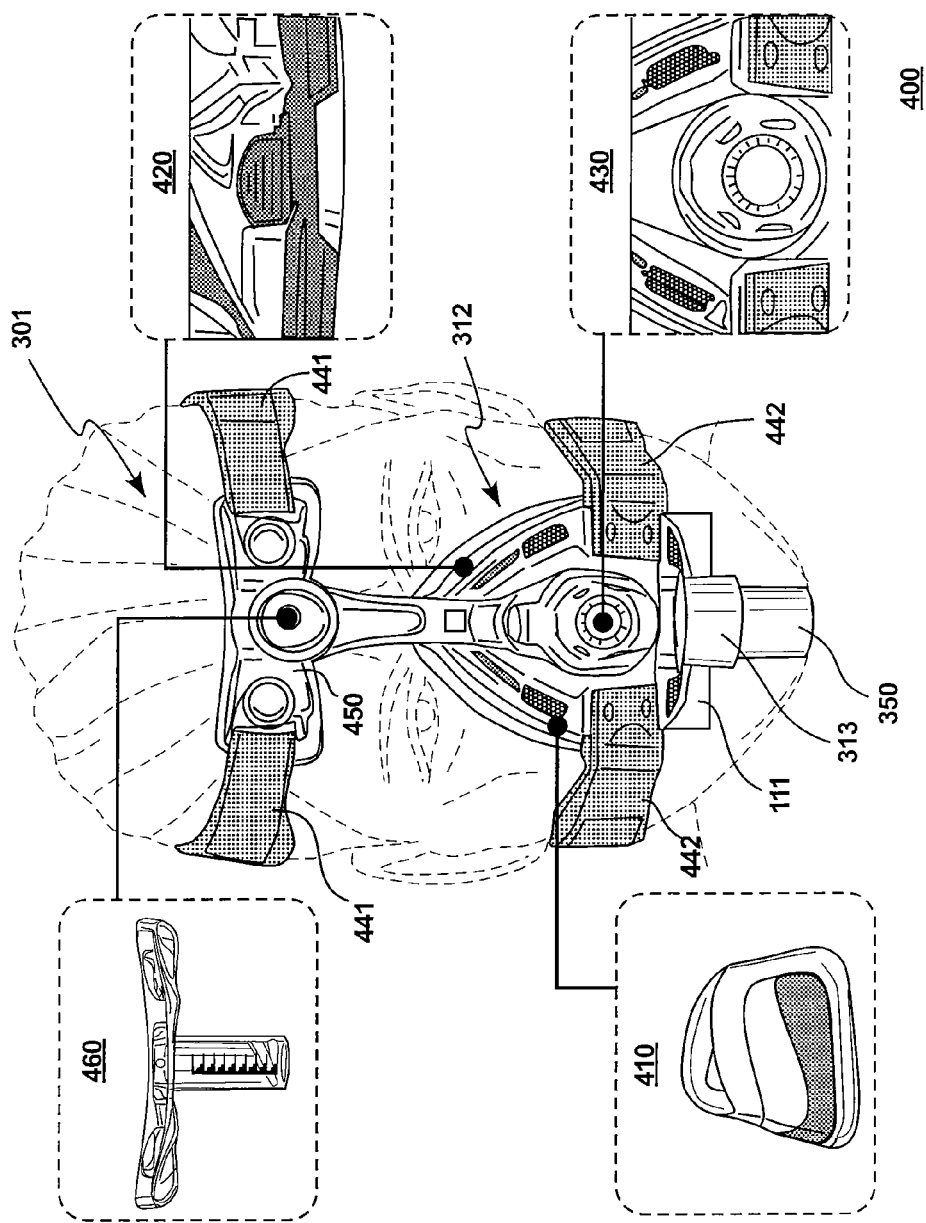
FIG. 6 illustrates an anterior view of a first exemplary respiratory apparatus in accordance with an embodiment.

With reference now to FIG. 6, a first exemplary respiratory apparatus 400 in accordance with an embodiment is shown. First exemplary respiratory apparatus 400 is similar to respiratory device 310 in FIG. 5 in that first exemplary respiratory apparatus 400 includes airflow resistor 111 and coupling member 313 each coupled with or extending from contoured mask 312, wherein hose 350 may be attached to coupling member 313. Additionally, first exemplary respiratory apparatus 400 includes a cushion 410 (e.g., a gel cushion) and a convertible frame 420, so as to provide an increased degree of comfort to a patient wearing first exemplary respiratory apparatus 400, as well as an exhalation port 430, which is configured to provide an escape route for exhaled air.

In one embodiment, upper and lower straps 441, 442 and a fastening member 450 are included, wherein fastening member 450 is configured to fasten a number of the straps together, such as to secure first exemplary respiratory apparatus 400 around a patient's head. Furthermore, an adjusting unit 460, which may include a fitting dial, may be provided to adjust a length of one or more of the straps, such as to tighten or loosen upper straps 441 when they are fastened together.

Figure 7:
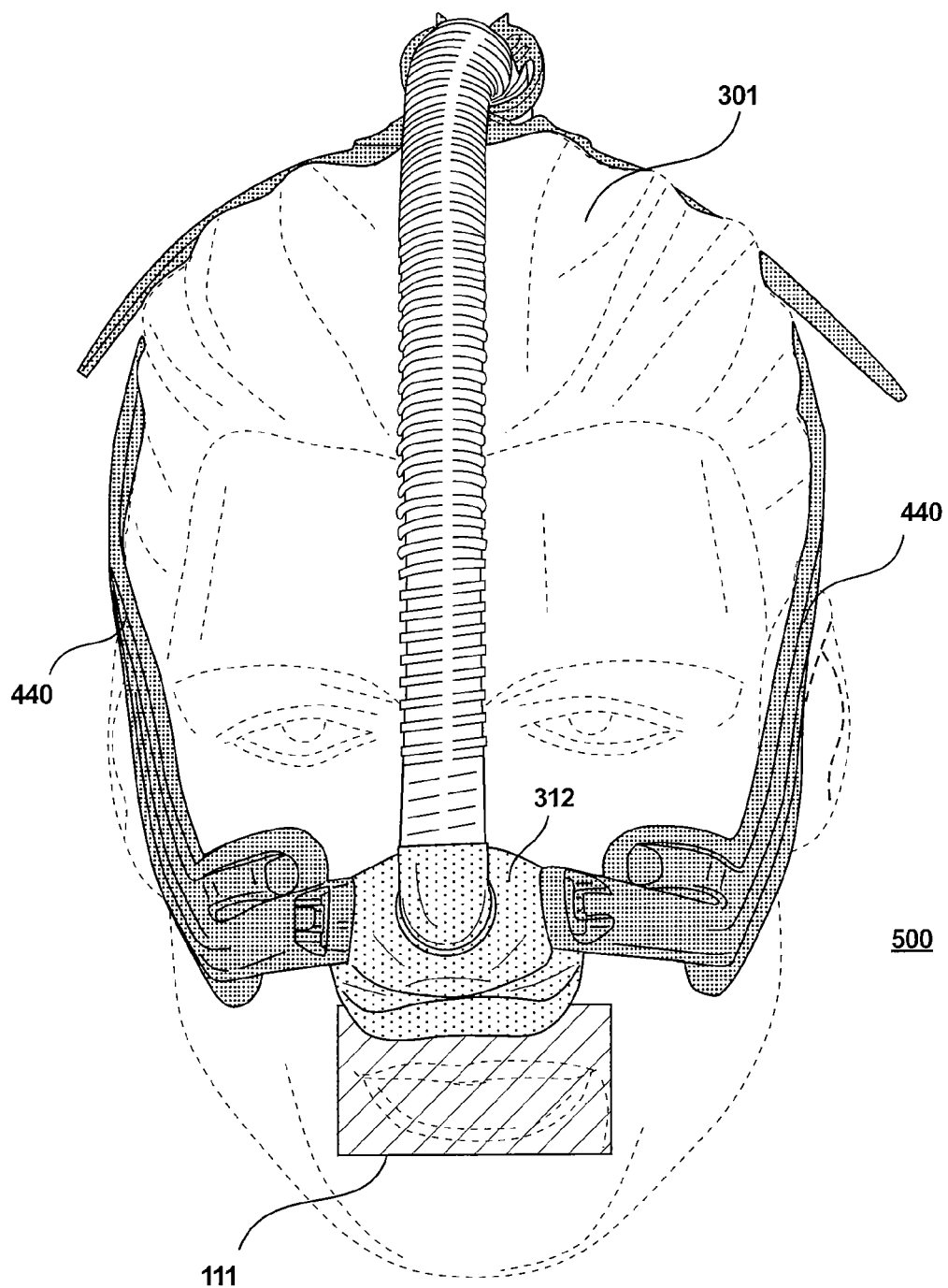
FIG. 7 illustrates an anterior view of a second exemplary respiratory apparatus in accordance with an embodiment.

With reference now to FIG. 7, a second exemplary respiratory apparatus 500 in accordance with an embodiment is shown. Second exemplary respiratory apparatus 500 includes airflow resistor 111 coupled with or extending from contoured mask 312. Additionally, second exemplary respiratory apparatus 500 includes straps 440, which may be fastened around a patient's head so as to hold contoured mask 312 and airflow resistor 111 in position on the patient's face.

Figure 8:
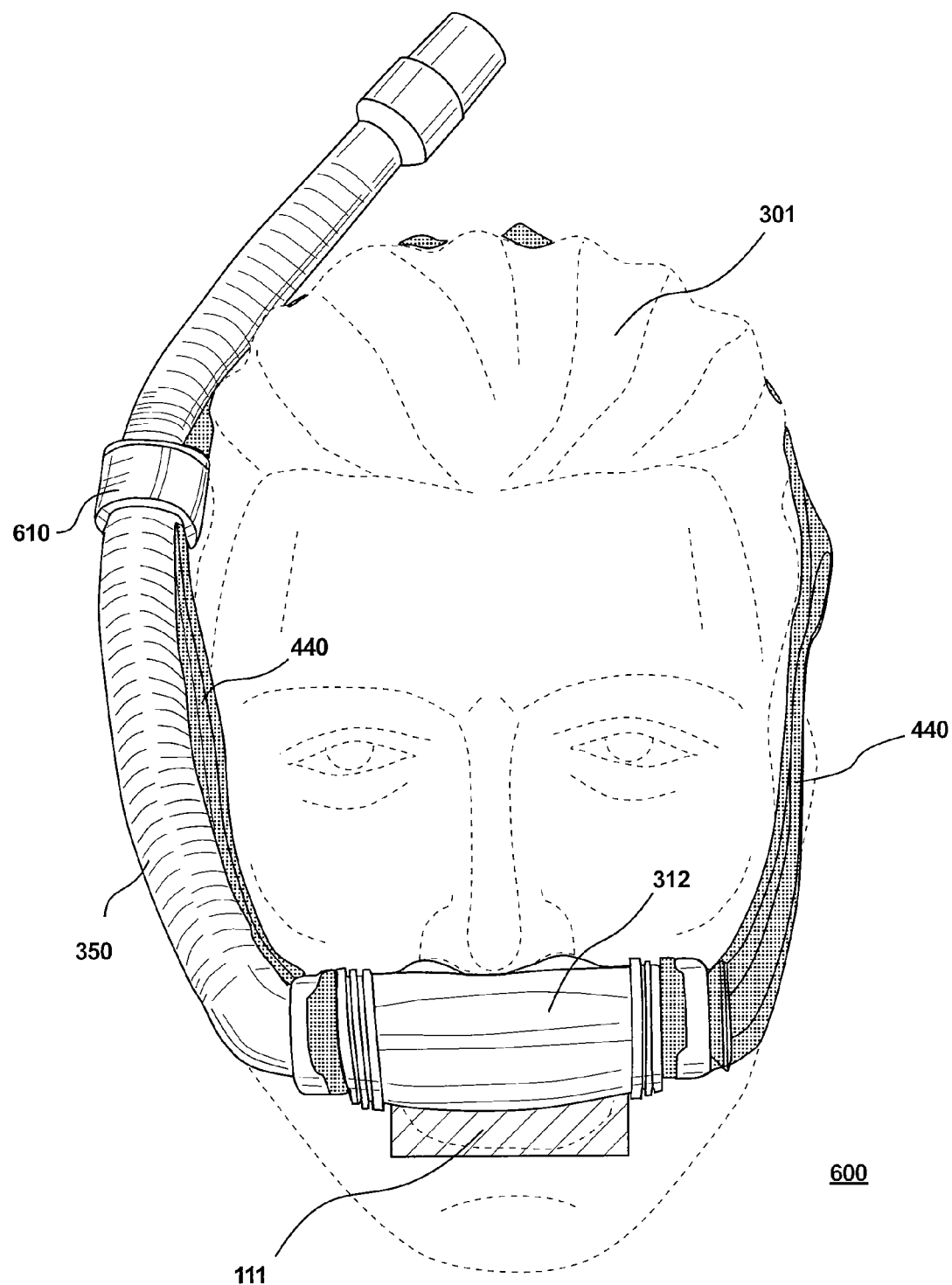
FIG. 8 illustrates an anterior view of a third exemplary respiratory apparatus in accordance with an embodiment.

With reference now to FIG. 8, a third exemplary respiratory apparatus 600 in accordance with an embodiment is shown. Similar to the apparatus shown in FIG. 7, third exemplary respiratory apparatus 600 includes airflow resistor 111 coupled with or extending from contoured mask 312, as well as straps 440, which may be fastened around a patient's head so as to hold contoured mask 312 and airflow resistor 111 in position on the patient's face. Additionally, third exemplary respiratory apparatus 600 includes a hose coupler 610, which is positioned to fasten hose 350 to one of straps 440 such that hose 350 may provide air to contoured mask 312 while simultaneously conforming to a shape of a patient's head, due to a degree of flexibility associated with hose 350, by being held adjacent to an outer portion of the patient's head.

Figure 9:
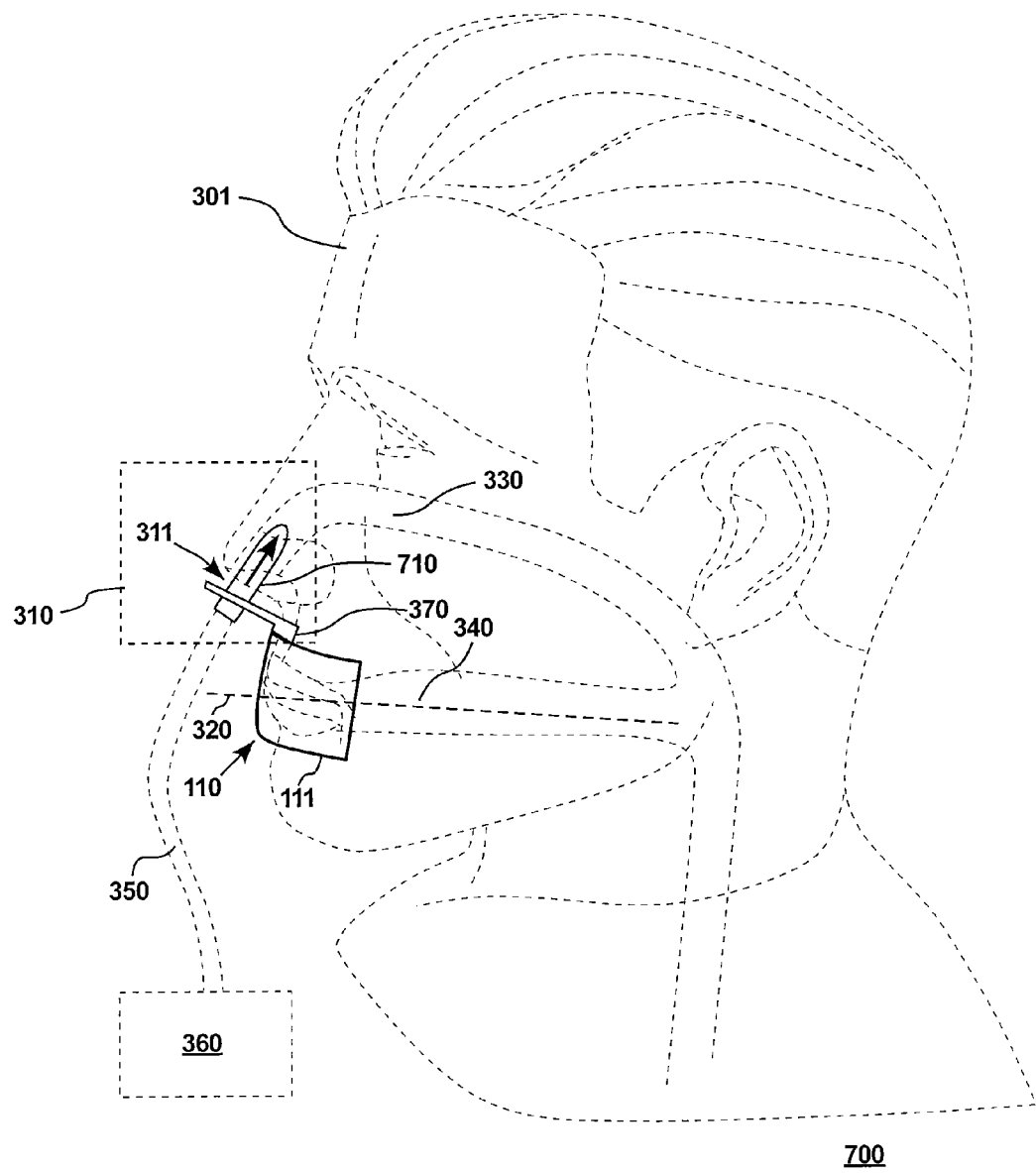
FIG. 9 illustrates a lateral view of a second exemplary respiratory configuration in accordance with an embodiment.

The foregoing notwithstanding, it is noted that while various exemplary embodiments discussed herein include a respiratory device having a contoured mask, the present technology is not limited to any particular type of respiratory device. For example, and with reference now to FIG. 9, a second exemplary respiratory configuration 700 in accordance with an embodiment is shown. In particular, nasal air intake member 311 of respiratory device 310 includes a hollow nasal plug 710 having a first end sized to couple with hose 350 and a second end sized to be inserted into and create a seal with nasal cavity 330, such as shown in FIG. 9. Additionally, extension 370 may be implemented to couple respiratory shield 110 with nasal air intake member 311, such as to suspend airflow resistor 111 adjacent to an opening of oral airflow cavity 340 along oral airflow axis 320 as shown. Furthermore, and with reference again to FIG. 3, one or more additional extensions 374 may also be implemented.

Figure 10:
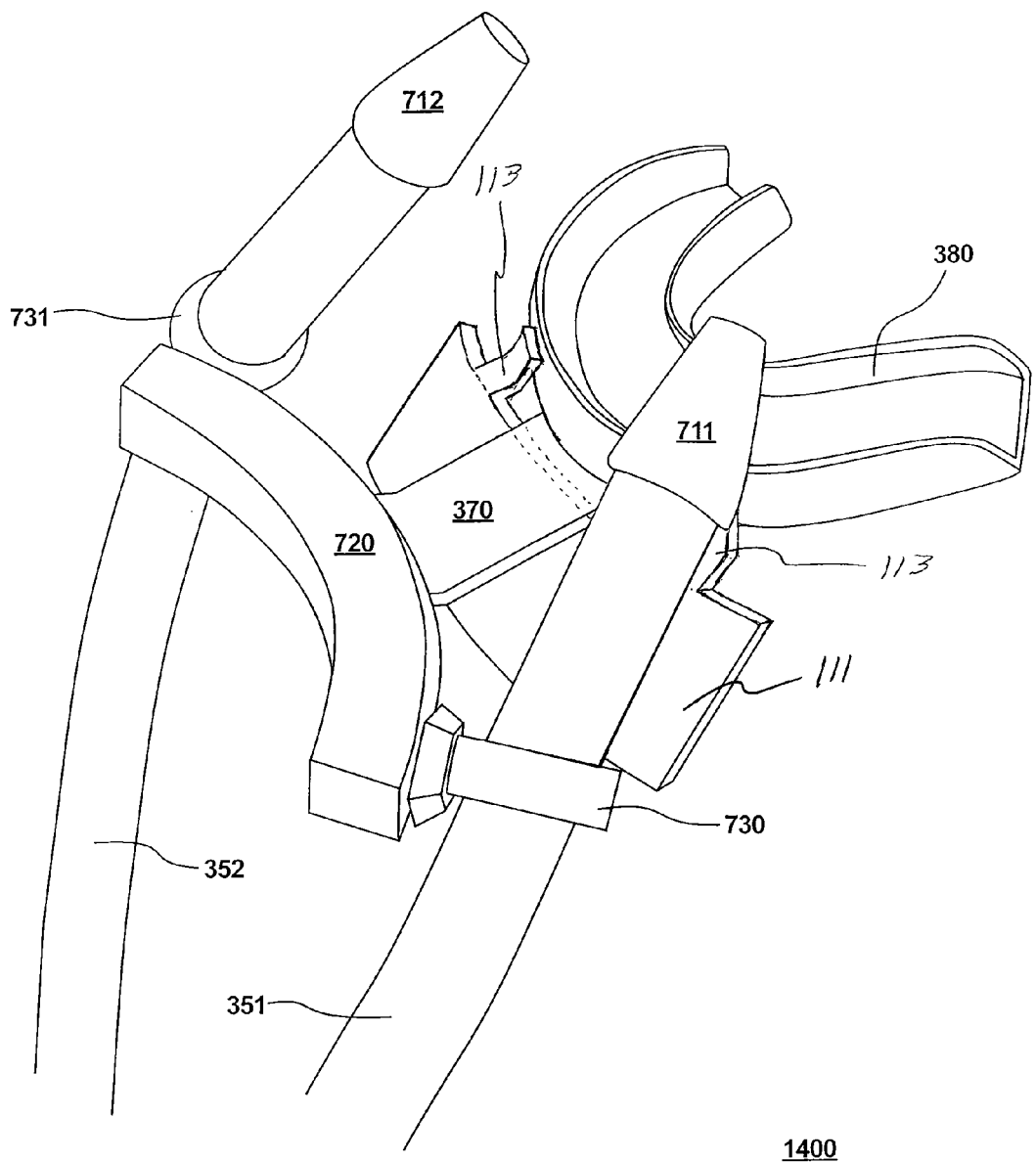
FIG. 10 illustrates a perspective view of a fourth exemplary respiratory apparatus in accordance with an embodiment.

With reference now to FIG. 10, a fourth exemplary respiratory apparatus 1400 in accordance with an embodiment is shown. Fourth exemplary respiratory apparatus 1400 includes a configuration for respiratory shield 110 similar to that discussed above (see, e.g., FIGS. 4A and 4B). In particular, airflow resistor 111 is coupled with dental anchor 380, such as by being directly coupled to dental anchor 380 by optional couplers 113, wherein airflow resistor 111 may be physically separated from extension 370. Alternatively, or in addition to the foregoing, airflow resistor 111 may optionally be affixed to extension 370, or extension 370 may be fabricated such that airflow resistor 111 extends there from.

Additionally, fourth exemplary respiratory apparatus 1400 further includes a base member 720, which is coupled with extension 370. Additionally, first and second clamps or coupling members 730, 731 are implemented to respectively couple first and second hoses 351, 352 to base member 720. Furthermore, first and second hollow nasal plugs 711, 712 are respectively coupled to first and second hoses 351, 352, wherein first and second hollow nasal plugs 711, 712 may be respectively fitted in different nostrils of a patient when fourth exemplary respiratory apparatus 1400 is worn. In this manner, first and second hoses 351, 352 are coupled with first and second hollow nasal plugs 711, 712 such that fourth exemplary respiratory apparatus 1400 is configured to route air provided by an air supply (not shown) to a patient simultaneously through multiple air channels.

With reference still to FIG. 10, an embodiment provides that fourth exemplary respiratory apparatus 1400 includes dental anchor 380 (as shown), which is positioned to anchor with a patient's upper dental jaw region. When a patient's mouth is opened, airflow resistor 111 is positioned to block a degree of airflow through the patient's mouth. As a result, the patient is discouraged from breathing through the mouth, and therefore instead breaths through a nasal cavity.

The foregoing notwithstanding, it is noted that other configurations may also be implemented, and that the present technology is not limited to the embodiment shown in FIG. 10. For example, as previously stated, it is further noted that dental anchor 380 is an optional component, and that various embodiments of the present technology may therefore be practiced without such a component.

Moreover, an embodiment provides that extension 370 is an optional component, such as where base member 720 is coupled directly to either airflow resistor 111 or dental anchor 380. Therefore, various embodiments of the present technology may be practiced without the implementation of such an extension member.

Furthermore, in one embodiment, base member 720 is an optional component. Consider the example where first and second hoses 351, 352 are coupled to either airflow resistor 111 or dental anchor 380, such as by being affixed thereto by first and second clamps or coupling members 730, 731 (see, e.g., FIG. 19, discussed infra). Therefore, various embodiments of the present technology may be practiced without the implementation of such a base member.

Figure 11:
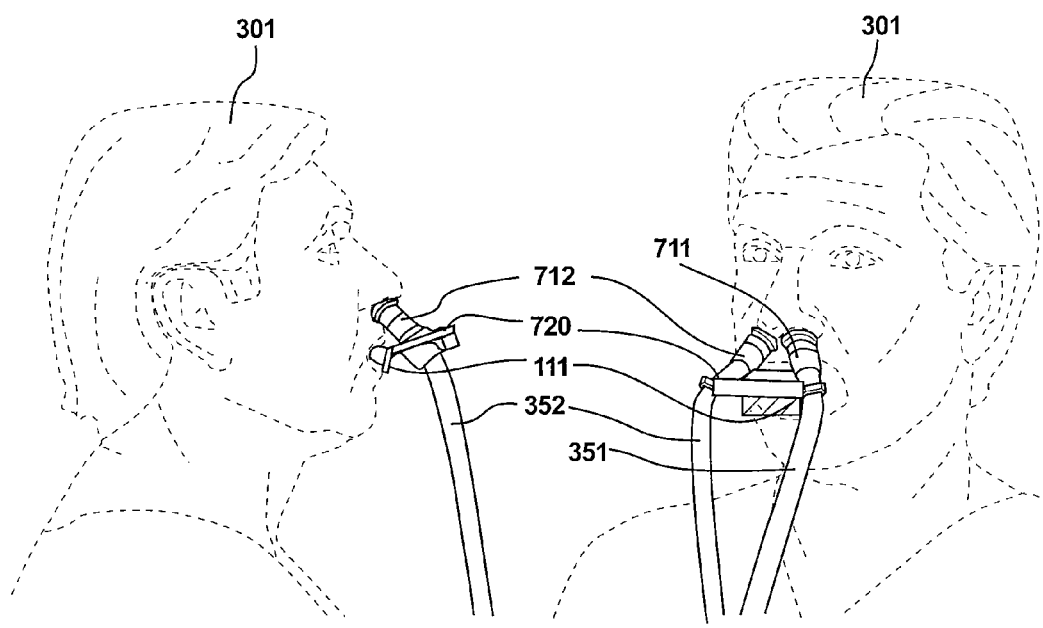
FIG. 11 illustrates anterior and lateral views of a third exemplary respiratory configuration in accordance with an embodiment.

With reference now to FIG. 11, a third exemplary respiratory configuration 800 in accordance with an embodiment is shown. For thoroughness of understanding, it may be seen that third exemplary respiratory configuration 800 illustrates an exemplary implementation of a respiratory device very similar to that shown in FIG. 10.

Figure 12:
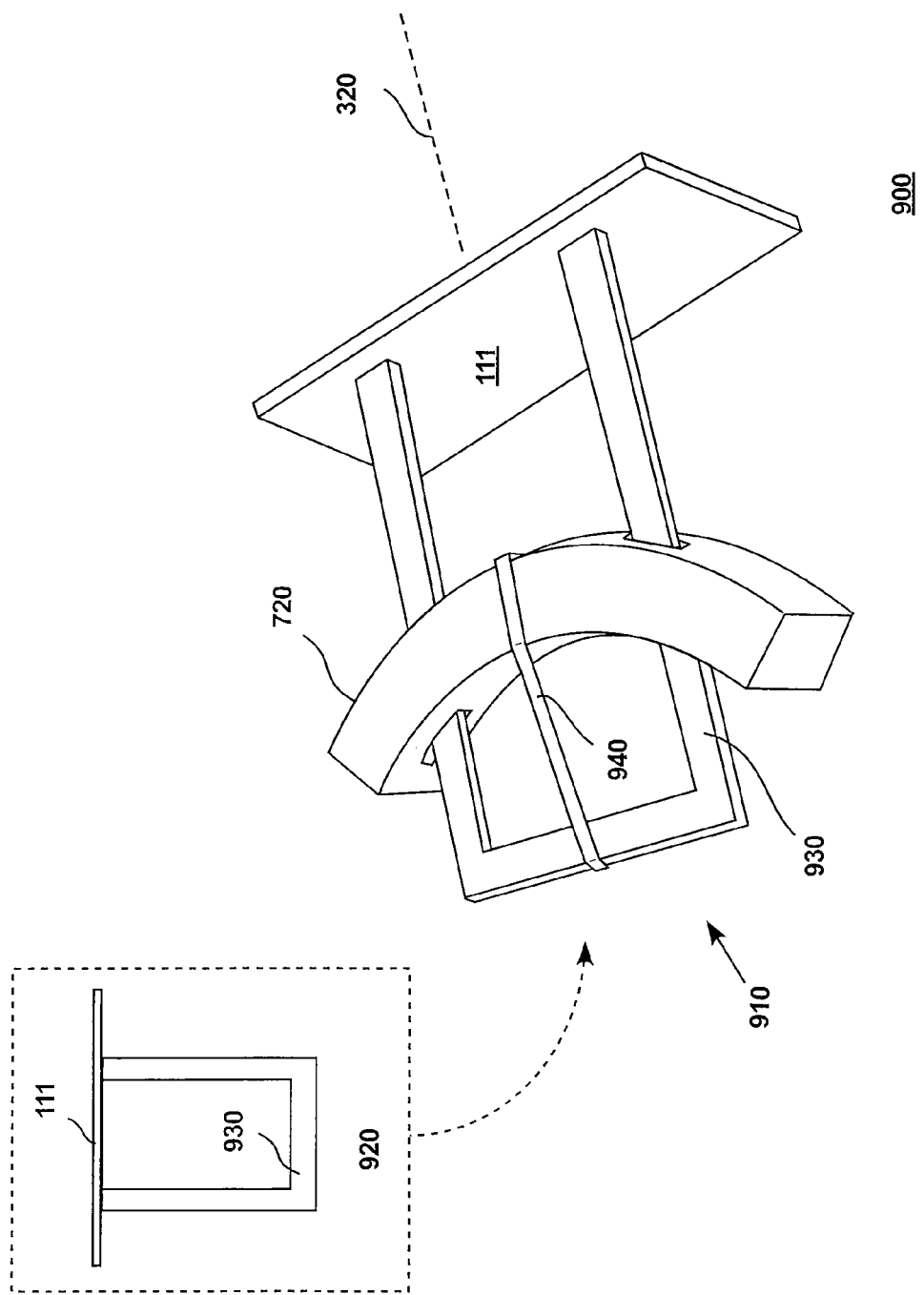
FIG. 12 illustrates a perspective view of a first exemplary configuration for an adjustable respiratory shield in accordance with an embodiment.

With reference now to FIG. 12, a first exemplary configuration 900 for an adjustable respiratory shield 910 in accordance with an embodiment is shown. In particular, first exemplary configuration 900 shows an adjustable slide mechanism that may be implemented, for example, with CPAP and other sleep/snoring devices. Adjustable respiratory shield 910 includes an airflow resistor assembly 920 having a rigid extension 930 coupled with or affixed to airflow resistor 111. Adjustable respiratory shield 910 further includes base member 720, wherein airflow resistor assembly 920 is moveably coupled with base member 720. In particular, and with reference to FIGS. 5 and 9, it is noted that airflow resistor assembly 920 is moveably coupled with base member 720 so as to be moveable along oral airflow axis 320 when adjustable respiratory shield 910 is coupled with respiratory device 310 and nasal air intake member 311 is positioned to direct airflow into nasal cavity 330.

With reference still to FIG. 12, it is noted that rigid extension 930 is moveably coupled with base member 720 such that rigid extension 930 may, for example, move or slide relative to base member 720. Such movement may result, for example, from a manual pressure exerted on airflow resistor assembly 920. However, in one embodiment, adjustable respiratory shield 910 is configured such that a position of airflow resistor assembly 920 relative to base member 720 automatically adjustable.

To illustrate, in an embodiment, an optional force exerting member 940 is coupled with both base member 720 and rigid extension 930, wherein force exerting member 940 is configured to exert a force on rigid extension 930 in a direction toward airflow resistor 111. In this manner, airflow resistor 111 may be automatically moved along oral airflow axis 320. Moreover, and with reference again to FIGS. 5 and 9, an embodiment provides that the size of rigid extension 930 and a magnitude of the force exerted on rigid extension 930 by force exerting member 940 are sufficient to apply airflow resistor 111 against a lip region of oral airflow cavity 340, outside of oral airflow cavity 340, within a preselected pressure range when adjustable respiratory shield 910 is coupled with respiratory device 310 and nasal air intake member 311 is positioned to direct airflow into nasal cavity 330.

The foregoing notwithstanding, it is noted that the present technology is not limited to any particular type of force exerting member. For example, force exerting member 940 may include a spring or an elastic element. Alternatively, other types of force exerting members may be implemented.

Figure 13:
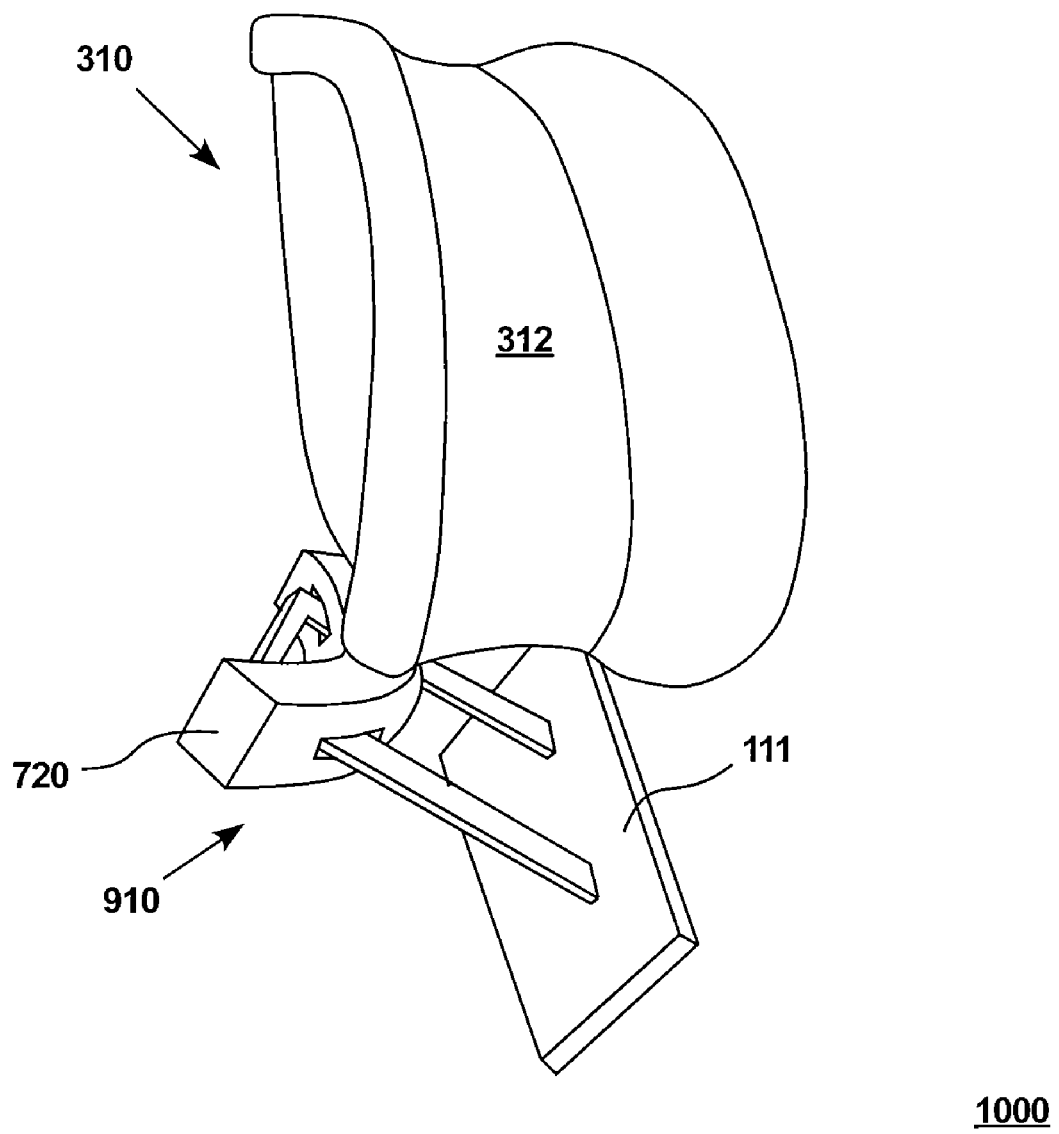
FIG. 13 illustrates a lateral view of a fifth exemplary respiratory apparatus in accordance with an embodiment.

With reference now to FIG. 13, a fifth exemplary respiratory apparatus 1000 in accordance with an embodiment is shown. Fifth exemplary respiratory apparatus 1000 includes respiratory device 310, wherein base member 720 of adjustable respiratory shield 910 is coupled with respiratory device 310 such that airflow resistor 111 is suspended relative to respiratory device 310.

It is noted that respiratory device 310 includes contoured mask 312, wherein cushion 410 is implemented such as to increase a degree of comfort associated with respiratory device 310. However, the present technology is not limited to any particular type of mask. Indeed, other types of masks may also be implemented.

Figure 14:
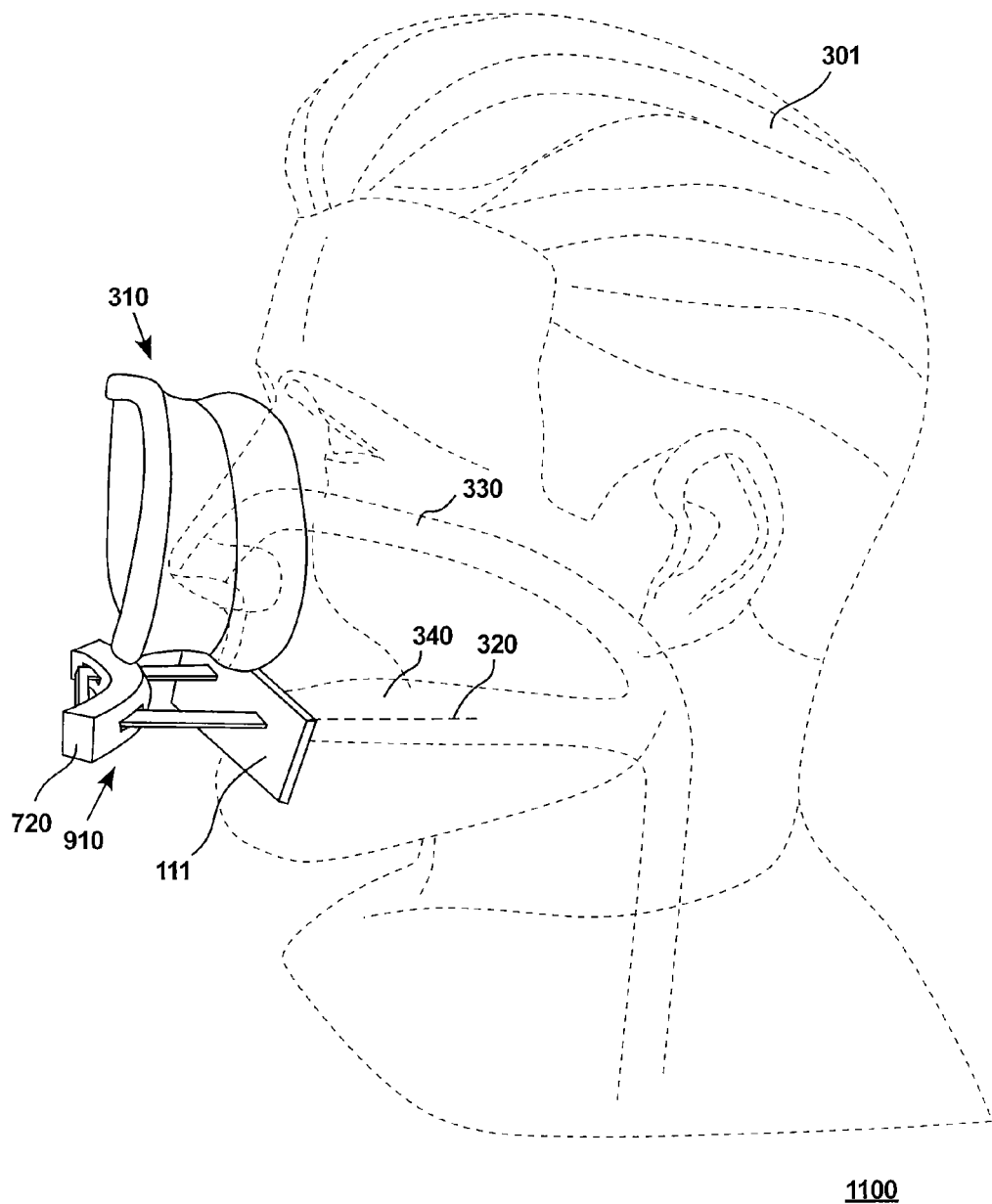
FIG. 14 illustrates a lateral view of a fourth exemplary respiratory configuration in accordance with an embodiment.

With reference now to FIG. 14, a fourth exemplary respiratory configuration 1100 in accordance with an embodiment is shown. In particular, respiratory device 310, which may include contoured mask 312 (such as shown in FIG. 13), is held against a patient's face so as to be positioned to direct airflow into nasal cavity 330. Additionally, base member 720 of adjustable respiratory shield 910 is coupled with respiratory device 310 such that airflow resistor 111 is suspended relative to respiratory device 310. In this manner, an embodiment provides that airflow resistor 111 is moveably coupled with base member 720 so as to be moveable along oral airflow axis 320 when adjustable respiratory shield 910 is coupled with respiratory device 310 and nasal air intake member 311 is positioned to direct airflow into nasal cavity 330.

The foregoing notwithstanding, an exemplary implementation provides that airflow resistor 111 is adjustable horizontally and/or vertically. Consider the example where airflow resistor 111 is moveably coupled with base member 720, such as previously explained, but wherein adjustable respiratory shield 910 is also moveably coupled with respiratory device 310. In this manner, airflow resistor 111 may be positioned along oral airflow axis 320 irrespective of a patient's unique physical size and shape, and consequently, the same device may be utilized by patients of different sizes and shapes (e.g., youths and adults).

Figure 15:
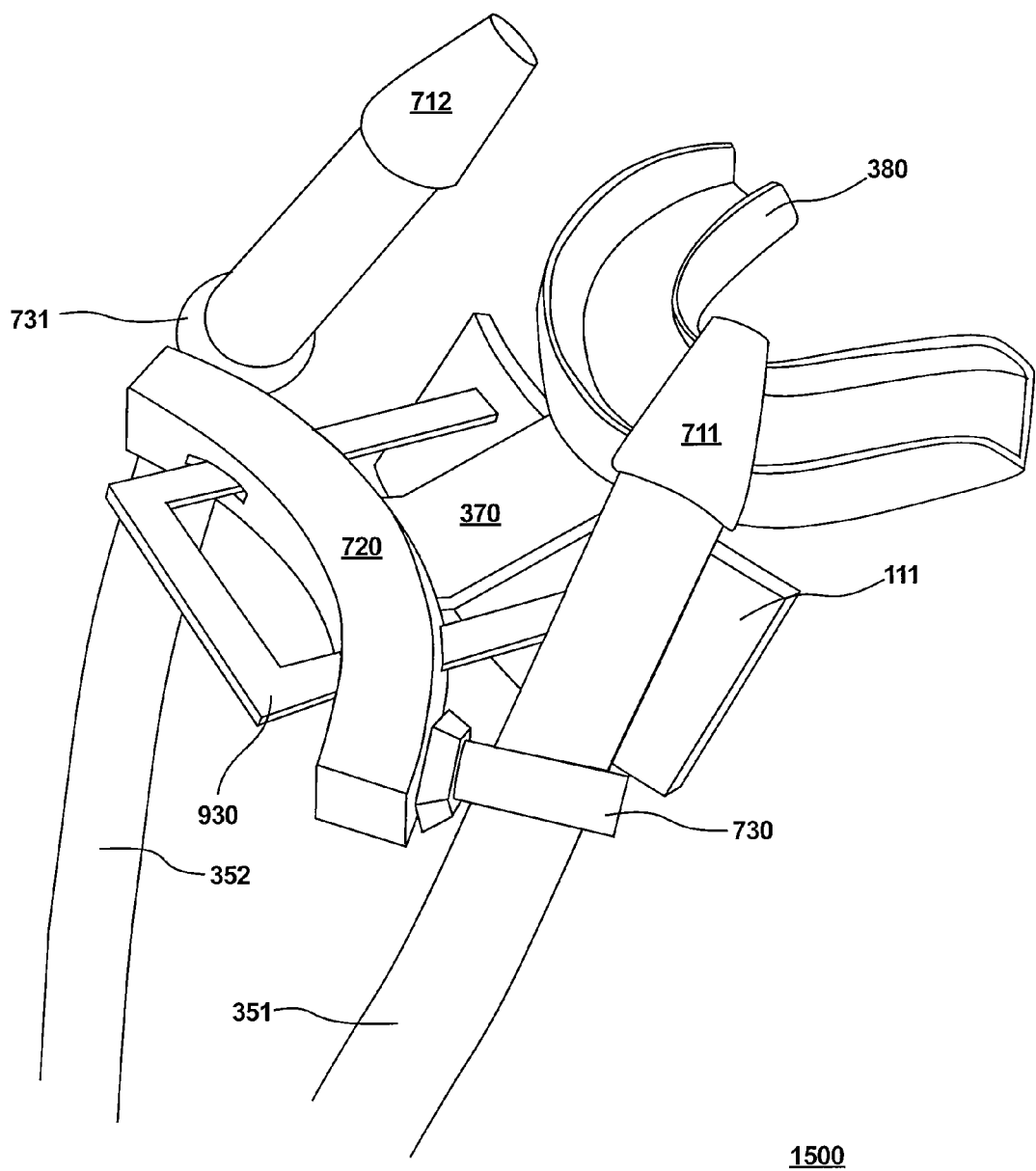
FIG. 15 illustrates a perspective view of a sixth exemplary respiratory apparatus in accordance with an embodiment.

With reference now to FIG. 15, a sixth exemplary respiratory apparatus 1500 in accordance with an embodiment is shown. Sixth exemplary respiratory apparatus 1500 is similar to the device shown in FIG. 10, except that airflow resistor 111 is movably coupled with base member 720. For example, rigid extension 930 may be included, as previously discussed, to slide relative to base member 720 such that airflow resistor 111 may be displaced along an oral airflow axis (not shown, but see, e.g., the discussion of FIG. 12 above).

In one embodiment, sixth exemplary respiratory apparatus 1500 also includes dental anchor 380 (as shown), which is positioned to anchor with a patient's upper dental jaw region. When a patient's mouth is opened, airflow resistor 111 is positioned to block a degree of airflow through the patient's mouth. As a result, the patient is discouraged from breathing through the mouth, and therefore instead breaths through a nasal cavity.

The foregoing notwithstanding, it is noted that other implementations of a dental anchor may also be implemented, and that the present technology is not limited to the specific configuration shown in FIG. 15. Moreover, as previously stated, it is further noted that dental anchor 380 is an optional component, and that various embodiments of the present technology may therefore be practiced without such a component.

Figure 16A:
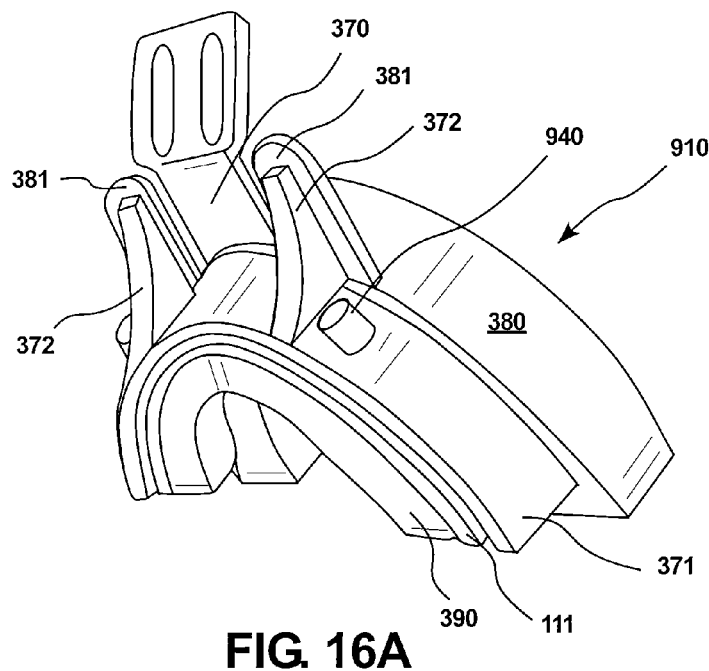
FIGS. 16A-16C illustrate perspective views of a second exemplary configuration for an adjustable respiratory shield in accordance with an embodiment.
Figure 16B:
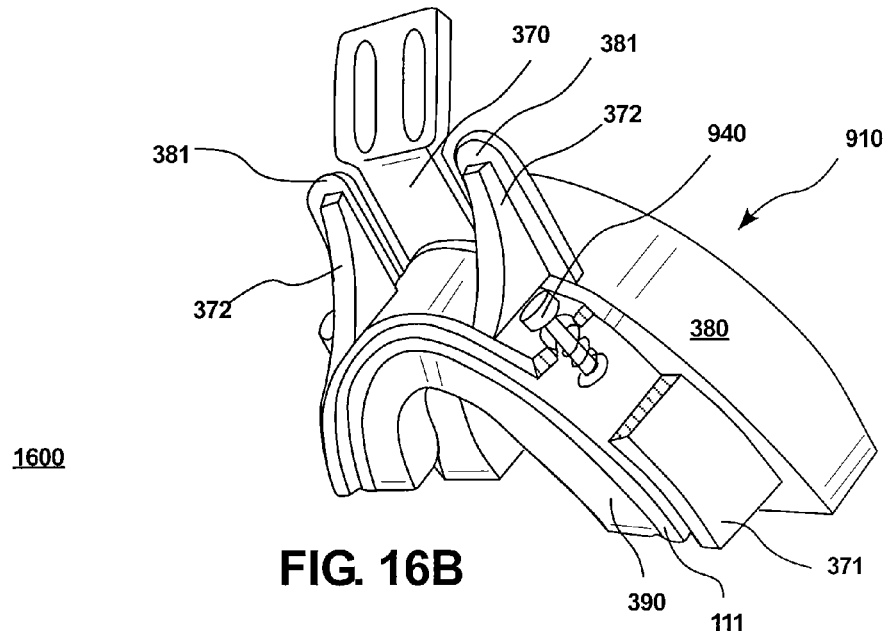
Figure 16C:
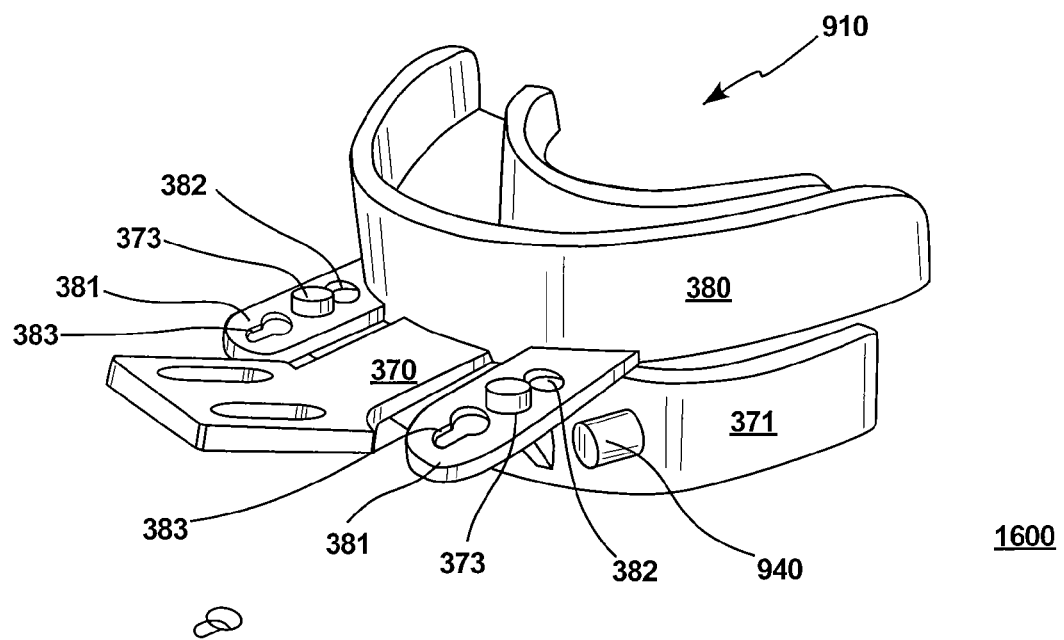

With reference now to FIGS. 16A-16C, a second exemplary configuration 1600 for adjustable respiratory shield 910 in accordance with an embodiment is shown. Adjustable respiratory shield 910 includes dental anchor 380 having grooved hinges 381 extending there from, wherein dental anchor 380 is coupled with extension 370. Adjustable respiratory shield 910 further includes a vertical base member 371 having notched hinges 372 extending there from, wherein notched hinges 372 have notches 373 sized to fit into grooves 382 of grooved hinges 381 so as to securely couple together vertical base member 371 and dental anchor 380. Furthermore, additional grooves 383 may also be presented in grooved hinges 381 such that a position of vertical base member 371 relative to dental anchor 380 may be adjusted by placing notches 373 through additional grooves 383 rather than through grooves 382.

In an embodiment, airflow resistor 111 is moveably coupled with vertical base member 371. In particular, a number of force exerting members 940 are coupled with both airflow resistor 111 and vertical base member 371, wherein force exerting members 940 are configured to push airflow resistor 111 in a direction away from vertical base member 371. In this manner, airflow resistor 111 may be pushed toward a patient's mouth when dental anchor 380 is anchored with a patient's jaw.

In one embodiment, an absorbent material 390 is coupled with airflow resistor 111. Absorbent material 390 may be configured to absorb a degree of force so as to provide, for example, a degree of comfort to a patient when airflow resistor 111 is pressed against the patient's face. Additionally, an embodiment provides that absorbent material 390 is a liquid absorbent material configured to absorb an amount of liquid, such as sweat and saliva emitted by a patient.

Thus, in an embodiment, adjustable respiratory shield 910 incorporates a CPAP dental appliance, which fits onto the patient's upper dental arch, with a mouth shield contained with a resilient member to maintain comfortable pressure against the open mouth area. The mouth shield may have some degree of porosity or no porosity, depending on whether a controlled degree of airflow through the device may be beneficial to the treatment.

The foregoing notwithstanding, an embodiment provides that adjustable respiratory shield 910 does not include dental anchor 380. Consider the example where extension 370 is coupled with a respiratory device while vertical base member 371 is attached to extension 370 rather than to dental anchor 380. It is therefore noted that dental anchor 380 is an optional component that may or may not be implemented.

Figure 17:
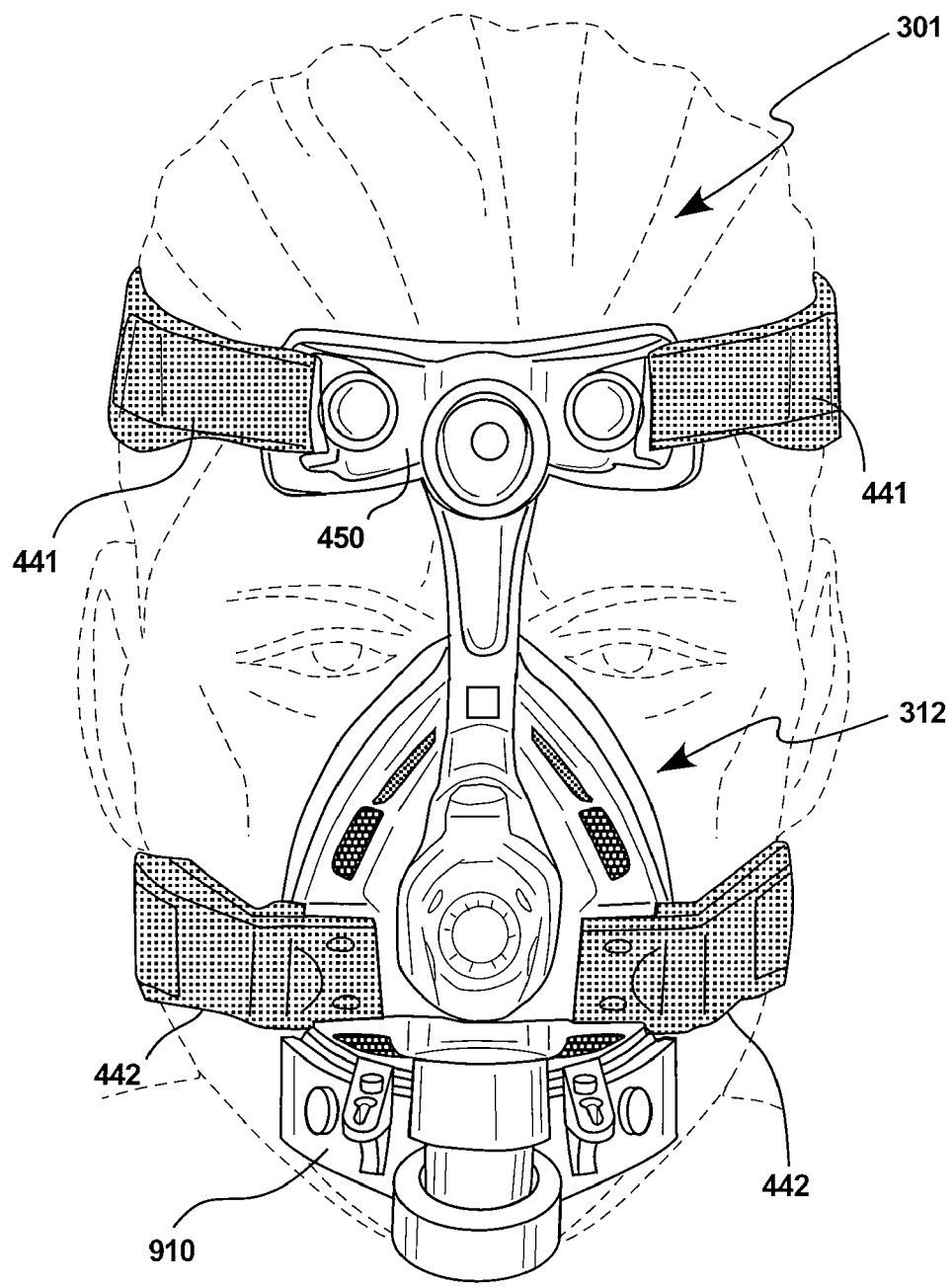
FIG. 17 illustrates an anterior view of a seventh exemplary respiratory apparatus in accordance with an embodiment.

With reference now to FIG. 17, a seventh exemplary respiratory apparatus 1700 in accordance with an embodiment is shown. It is noted that seventh exemplary respiratory apparatus 1700 is similar in structure to the device shown in FIG. 6. However, seventh exemplary respiratory apparatus 1700 also includes adjustable respiratory shield 910, which is coupled with contoured mask 312.

Figure 18:
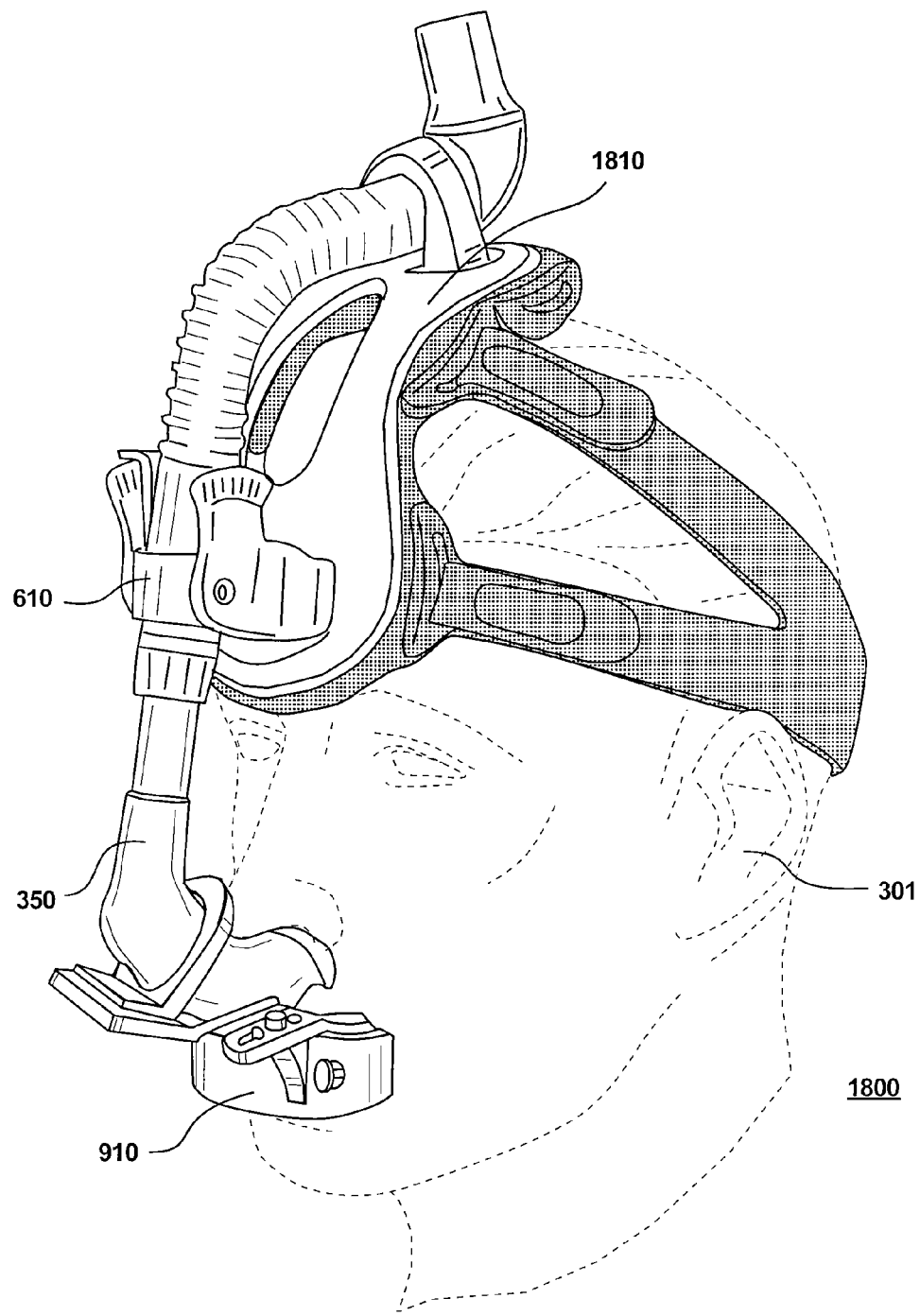
FIG. 18 illustrates a perspective view of an eighth exemplary respiratory apparatus in accordance with an embodiment.

With reference now to FIG. 18, an eighth exemplary respiratory apparatus 1800 in accordance with an embodiment is shown. Eighth exemplary respiratory apparatus 1800 includes a strap assembly 1810 configured to adhere to a patient's head. Additionally, hose coupler 610 is coupled with strap assembly 1810, wherein hose coupler 610 is configured to hold or support hose 350 relative to strap assembly 1810. Furthermore, adjustable respiratory shield 910 is coupled with hose 350. In this manner, adjustable respiratory shield 910 may be suspended relative to strap assembly 1810.

In one embodiment, adjustable respiratory shield 910, such as shown in FIG. 17 and/or FIG. 18, is configured as shown in FIGS. 16A-16C. It is noted, however, that various other configures for adjustable respiratory shield 910 may also be adopted, such as where adjustable respiratory shield 910 does not include dental anchor 380.

It is noted that various embodiments of the present technology may be implemented without certain components discussed herein. For example, and as previously discussed, extension 370 is an optional component that may be excluded from a device fabricated in accordance with various principles described herein. Additionally, base member 720 is also one such optional component. For purposes of illustration, an exemplary arrangement will now be described in which these two optional components are excluded, although the present technology is not limited to the following arrangement.

Figure 19:
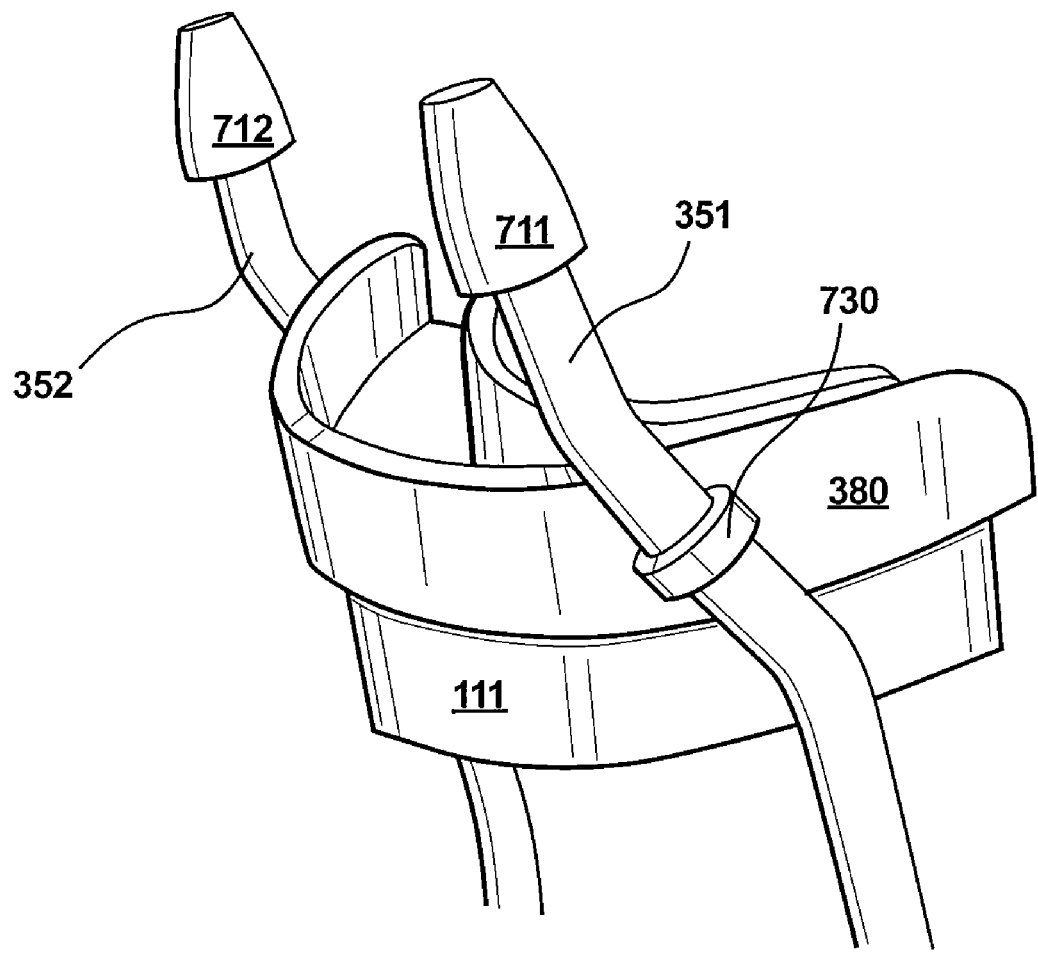
FIG. 19 illustrates a perspective view of a ninth exemplary respiratory apparatus in accordance with an embodiment.

With reference now to FIG. 19, a ninth exemplary respiratory apparatus 1900 in accordance with an embodiment is shown. Ninth exemplary respiratory apparatus 1900 includes dental anchor 380 with airflow resistor 111 extending there from. Additionally, first and second hoses 351, 352 are coupled with dental anchor 380, such as by first and second clamps or coupling members 730, 731 (the latter not being shown). Thus, an embodiment provides that base member 720 and/or extension 370 may be omitted from various embodiments of the present technology. Indeed, it is noted that the present technology includes obvious variations of the exemplary embodiments and implementations described herein.

Summary Concepts

It is noted that the foregoing discussion has presented at least the following concepts:

1. A respiratory shield sized to be coupled with a respiratory device having a nasal air intake member so as to be positioned along an oral airflow axis.

2. The respiratory shield of Concept 1, wherein the respiratory shield is sized to be coupled with the respiratory device so as to be positioned along the oral airflow axis when the nasal air intake member is positioned to inject air into a nasal cavity.

3. The respiratory shield of Concept 1, wherein the respiratory shield is sized to be coupled with the respiratory device so as to be positioned adjacent to an opening of an oral cavity and resist a degree of airflow through the oral cavity when the nasal air intake member is positioned to direct airflow into a nasal cavity.

4. The respiratory shield of Concept 1, including or comprising:

an airflow resistor sized to be applied against a lip region of an oral cavity, outside of the oral cavity, within a preselected pressure range when the respiratory shield is coupled with the respiratory device and the nasal air intake member is positioned to direct airflow into a nasal cavity.

5. The respiratory shield of Concept 4, wherein the airflow resistor is porous.

6. The respiratory shield of Concept 4, further including or comprising:

a liquid absorbent material coupled with the airflow resistor.

7. The respiratory shield of Concept 4, wherein the airflow resistor includes or comprises a liquid absorbent material.

8. The respiratory shield of Concept 4, further including or comprising:

an air seal coupled with the airflow resistor.

9. The respiratory shield of Concept 1, including or comprising:

a base member; and an airflow resistor assembly moveably coupled with the base member so as to be moveable along the oral airflow axis when the respiratory shield is coupled with the respiratory device and the nasal air intake member is positioned to direct airflow into a nasal cavity.

10. The respiratory shield of Concept 9, wherein the airflow resistor assembly includes or comprises:

an airflow resistor;

a rigid extension coupled with the airflow resistor and moveably coupled with the base member; and a force exerting member coupled with the base member and the rigid extension, the force exerting member positioned to exert a force on the rigid extension in a direction toward the airflow resistor.

11. The respiratory shield of Concept 10, wherein a size of the rigid extension and a magnitude of the force are sufficient to apply the airflow resistor against a lip region of the oral cavity, outside of the oral cavity, within a preselected pressure range when the respiratory shield is coupled with the respiratory device and the nasal air intake member is positioned to direct airflow into a nasal cavity.

12. The respiratory shield of Concept 10, wherein the force exerting member includes or comprises:

a spring or an elastic element.

13. The respiratory shield of Concept 1, wherein the respiratory shield includes or comprises:

a dental anchor sized and positioned to anchor with a dental region when the respiratory shield is coupled with the respiratory device and the nasal air intake member is positioned to direct airflow into a nasal cavity.

14. A respiratory shield including or comprising:

a base member;

an airflow resistor;

a rigid extension associated with the airflow resistor and the base member; and a force exerting member associated with the base member and the rigid extension, the force exerting member positioned to exert a force on the rigid extension in a direction toward the airflow resistor.

15. A respiratory device including or comprising:

a nasal air intake member; and a respiratory shield associated with the nasal air intake member so as to be positioned to resist a degree of airflow through an oral cavity when the nasal air intake member is positioned to direct airflow into a nasal cavity.

16. The respiratory device of Concept 15, wherein the respiratory shield includes or comprises:

an airflow resistor coupled with the nasal air intake member and sized to be applied against a lip region of the oral cavity within a preselected pressure range when the nasal air intake member is positioned to direct airflow into the nasal cavity.

17. The respiratory device of Concept 15, wherein the respiratory shield includes or comprises:

a base member coupled with the nasal air intake member; and an airflow resistor assembly moveably coupled with the base member so as to be moveable along an oral airflow axis when the nasal air intake member is positioned to direct airflow into the nasal cavity.

18. The respiratory device of Concept 17, wherein the airflow resistor assembly includes or comprises:

an airflow resistor;

a rigid extension coupled with the airflow resistor and moveably coupled with the base member; and a force exerting member coupled with the base and the rigid extension, the force exerting member positioned to exert a force on the rigid extension in a direction toward the airflow resistor.

19. The respiratory device of Concept 18, wherein a size of the rigid extension and a magnitude of the force are sufficient to apply the airflow resistor against a lip region of the oral cavity within a preselected pressure range when the nasal air intake member is positioned to direct airflow into the nasal cavity.

20. The respiratory device of Concept 18, wherein the force exerting member includes or comprises:

a spring or an elastic element.

21. The respiratory device of Concept 15, wherein the respiratory shield includes or comprises:

a dental anchor sized and positioned to anchor with a dental region when the nasal air intake member is positioned to direct airflow into the nasal cavity.

Although various exemplary embodiments of the present technology are described herein in a language specific to structural features, the subject matter defined in the appended claims is not necessarily limited to the specific features described above. Rather, the specific features described above are disclosed as exemplary forms of implementing the claims.

What is claimed is:

1. A respiratory shield comprising:
   a base member;
   an airflow resistor sized to be coupled with a respiratory device having a nasal air intake member so as to be positioned along an oral airflow axis of an oral cavity when said nasal air intake member is positioned to direct airflow into a nasal cavity;
   a rigid extension associated with said airflow resistor and said base member; and
   a force exerting member associated with said base member and said rigid extension, said force exerting member positioned to exert a force on said rigid extension in a direction toward said airflow resistor, and:
   i. said force exerting member sized to expand or contract so as to increase or decrease in length and exert said force on said rigid extension in said direction toward said airflow resistor; or
   ii. said force exerting member including a spring or an elastic element.

2. A respiratory device comprising:
a nasal air intake member; and
the respiratory shield of claim 1, said respiratory shield sized and coupled with said nasal air intake member so as to be positioned to resist a degree of airflow through said oral cavity when said nasal air intake member is positioned to direct airflow into said nasal cavity.

3. The respiratory device of claim 2, wherein said respiratory shield comprises:
said airflow resistor coupled with said nasal air intake member and sized to be applied against a lip region of said oral cavity within a preselected pressure range when said nasal air intake member is positioned to direct airflow into said nasal cavity; and
one or more straps associated with said nasal air intake member and sized to extend around a head of a patient and secure said nasal air intake member to a face of said patient.

4. The respiratory device of claim 2, wherein said respiratory shield comprises:
said base member coupled with said nasal air intake member; and
an airflow resistor assembly moveably coupled with said base member so as to be moveable along said oral airflow axis when said nasal air intake member is positioned to direct airflow into said nasal cavity.

5. The respiratory device of claim 4, wherein said airflow resistor assembly comprises:
said airflow resistor;
said rigid extension coupled with said airflow resistor and moveably coupled with said base member; and
said force exerting member coupled with said base member and said rigid extension.

6. The respiratory device of claim 5, wherein a size of said rigid extension and a magnitude of said force are sufficient to apply said airflow resistor against a lip region of said oral cavity within a preselected pressure range when said nasal air intake member is positioned to direct airflow into said nasal cavity.

7. The respiratory device of claim 5, wherein said force exerting member comprises:
said spring or said elastic element.

8. The respiratory shield of claim 1, wherein said force exerting member is positioned to automatically move said airflow resistor.

9. The respiratory shield of claim 1, wherein said force exerting member is sized to expand or contract so as to increase or decrease in length and exert said force on said rigid extension in said direction toward said airflow resistor.

10. The respiratory shield of claim 1, wherein said respiratory shield is sized to be coupled with said respiratory device so as to be positioned along said oral airflow axis when said nasal air intake member is positioned to inject air into said nasal cavity, said force exerting member being associated with said airflow resistor and positioned to automatically move said airflow resistor.

11. The respiratory shield of claim 1, wherein said respiratory shield is sized to be coupled with said respiratory device so as to be positioned adjacent to an opening of said oral cavity and resist a degree of airflow through said oral cavity when said nasal air intake member is positioned to direct airflow into said nasal cavity, said force exerting member including a helical spring element positioned to expand or contract so as to move said airflow resistor.

12. The respiratory shield of claim 1, wherein said airflow resistor is sized to be applied against a lip region of said oral cavity, outside of said oral cavity, within a preselected pressure range when said respiratory shield is coupled with said respiratory device and said nasal air intake member is positioned to direct airflow into said nasal cavity, said airflow resistor being adjustable both horizontally and vertically.

13. The respiratory shield of claim 12, wherein said airflow resistor is porous.

14. The respiratory shield of claim 12, further comprising:
an air seal; and
a liquid absorbent material coupled between said airflow resistor and said air seal.

15. The respiratory shield of claim 12, wherein said airflow resistor comprises a liquid absorbent material.

16. The respiratory shield of claim 12, further comprising:
an air seal coupled with said airflow resistor.

17. The respiratory shield of claim 1 comprising:
an airflow resistor assembly moveably coupled with said base member so as to be moveable along said oral airflow axis when said respiratory shield is coupled with said respiratory device and said nasal air intake member is positioned to direct airflow into said nasal cavity.

18. The respiratory shield of claim 17, wherein said airflow resistor assembly comprises:
said airflow resistor;
said rigid extension coupled with said airflow resistor and moveably coupled with said base member; and
said force exerting member coupled with said base member and said rigid extension.

19. The respiratory shield of claim 18, wherein a size of said rigid extension and a magnitude of said force are sufficient to apply said airflow resistor against a lip region of said oral cavity, outside of said oral cavity, within a preselected pressure range when said respiratory shield is coupled with said respiratory device and said nasal air intake member is positioned to direct airflow into said nasal cavity, said rigid extension being generally "U" shaped.

20. The respiratory shield of claim 18, wherein said force exerting member comprises:
said spring or said elastic element.

* * * * *